US010874825B2

(12) United States Patent
Yin et al.

(10) Patent No.: US 10,874,825 B2
(45) Date of Patent: Dec. 29, 2020

(54) URINARY CATHETER

(71) Applicant: C. R. Bard, Inc., Franklin Lakes, NJ (US)

(72) Inventors: Zhihui Yin, Lilburn, GA (US); Brian Chapman, Covington, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 266 days.

(21) Appl. No.: 15/724,879

(22) Filed: Oct. 4, 2017

(65) Prior Publication Data

US 2018/0021481 A1 Jan. 25, 2018

Related U.S. Application Data

(63) Continuation-in-part of application No. 15/506,723, filed as application No. PCT/US2015/047026 on Aug. 26, 2015.

(Continued)

(51) Int. Cl.
*A61M 25/00* (2006.01)
*A61L 29/08* (2006.01)
(Continued)

(52) U.S. Cl.
CPC ....... *A61M 25/0017* (2013.01); *A61L 29/085* (2013.01); *A61L 29/14* (2013.01);
(Continued)

(58) Field of Classification Search
None
See application file for complete search history.

(56) References Cited

U.S. PATENT DOCUMENTS

| 734,498 A | 7/1903 | Bachler |
| 1,131,865 A | 3/1915 | Putnam et al. |

(Continued)

FOREIGN PATENT DOCUMENTS

| BR | PI0803737 A2 | 1/2010 |
| CA | 763930 A | 7/1967 |

(Continued)

OTHER PUBLICATIONS

Akzo Nobel, "Ethomeen C/25 technical data sheet" Mar. 10, 2009.

(Continued)

*Primary Examiner* — Adam Marcetich
(74) *Attorney, Agent, or Firm* — Rutan & Tucker LLP

(57) ABSTRACT

A urinary catheter and container are described. The urinary catheter may have a catheter shaft attached to a handle, and a coating disposed on an outer surface of the catheter shaft. The coating may include a hydrogel, water and/or glycerin, and a polyethylene glycol (PEG). The PEG may have a molecular weight equal to or less than 600, for example one or more of polyethylene glycol (PEG) 300 and PEG 400. The coating may be applied in a wet state and remain wet for an extended period of time in the container, thereby obviating the need for a lubricant, such as a water sachet or gel package, to accompany the catheter in the container. The container may include a gas impermeable foil material. The container may include an adhesive tab covering a perforated section, the adhesive tab including a pull loop.

12 Claims, 13 Drawing Sheets

Related U.S. Application Data

(60) Provisional application No. 62/042,125, filed on Aug. 26, 2014.

(51) Int. Cl.
*A61L 29/14* (2006.01)
*A61M 25/01* (2006.01)

(52) U.S. Cl.
CPC ......... *A61L 29/145* (2013.01); *A61M 25/002* (2013.01); *A61M 25/007* (2013.01); *A61M 25/0045* (2013.01); *A61M 25/0136* (2013.01); *A61L 29/08* (2013.01); *A61L 29/141* (2013.01); *A61L 2400/10* (2013.01); *A61L 2420/08* (2013.01); *A61M 25/0009* (2013.01); *A61M 2025/0046* (2013.01)

(56) References Cited

U.S. PATENT DOCUMENTS

| | | |
|---|---|---|
| 1,235,142 A | 7/1917 | Ichilian |
| 1,304,396 A | 5/1919 | Smith |
| 1,643,289 A | 9/1927 | Peglay |
| 1,661,494 A | 3/1928 | Nielsen |
| 1,876,229 A | 9/1932 | Herzog |
| 2,043,630 A | 6/1936 | Raiche |
| 2,213,210 A | 9/1940 | Egbert |
| 2,228,992 A | 1/1941 | Fry |
| 2,230,226 A | 2/1941 | Auzin |
| 2,248,934 A | 7/1941 | Auzin |
| 2,285,502 A | 6/1942 | Dreyfus |
| 2,308,484 A | 1/1943 | Auzin et al. |
| 2,314,262 A | 3/1943 | Winder |
| 2,320,157 A | 5/1943 | Raiche |
| 2,322,858 A | 6/1943 | Limbert et al. |
| 2,330,399 A | 9/1943 | Winder |
| 2,330,400 A | 9/1943 | Winder |
| 2,389,831 A | 11/1945 | Welsh |
| 2,390,070 A | 12/1945 | Auzin |
| 2,481,488 A | 9/1949 | Auzin |
| 2,494,393 A | 1/1950 | Lamson |
| 2,610,626 A | 9/1952 | Edwards |
| 2,638,093 A | 5/1953 | Kulick |
| 2,649,619 A | 8/1953 | Killian |
| 2,649,854 A | 8/1953 | Salm |
| 2,690,595 A | 10/1954 | Raiche |
| 2,712,161 A | 7/1955 | Moss |
| 2,856,932 A | 10/1958 | Griffitts |
| 2,912,981 A | 11/1959 | Keough |
| 3,044,468 A | 7/1962 | Birtwell |
| 3,053,257 A | 9/1962 | Birtwell |
| 3,076,464 A | 2/1963 | Rosenberg |
| 3,169,527 A | 2/1965 | Sheridan |
| 3,211,151 A | 10/1965 | Foderick et al. |
| 3,304,353 A | 2/1967 | Harautuneian |
| 3,345,988 A | 10/1967 | Vitello |
| 3,394,704 A | 7/1968 | Dery |
| 3,394,705 A | 7/1968 | Abramson |
| 3,403,682 A | 10/1968 | McDonell |
| 3,409,016 A | 11/1968 | Foley |
| 3,434,869 A | 3/1969 | Davidson |
| 3,463,141 A | 8/1969 | Mozolf |
| 3,503,400 A | 3/1970 | Osthagen |
| 3,508,959 A | 4/1970 | Krahnke |
| 3,509,884 A | 5/1970 | Bell |
| 3,520,305 A | 7/1970 | Davis |
| 3,539,674 A | 11/1970 | Dereniuk et al. |
| 3,544,668 A | 12/1970 | Dereniuk |
| 3,548,805 A | 12/1970 | Datsenko |
| 3,556,294 A | 1/1971 | Walck et al. |
| 3,566,874 A | 3/1971 | Shepherd et al. |
| 3,593,713 A | 7/1971 | Bogoff et al. |
| 3,598,127 A | 8/1971 | Wepsic |
| 3,606,889 A | 9/1971 | Arblaster |
| 3,642,004 A | 2/1972 | Osthagen et al. |
| 3,646,929 A | 3/1972 | Bonnar |
| 3,648,704 A | 3/1972 | Jackson |
| 3,683,928 A | 8/1972 | Kuntz |
| 3,695,921 A | 10/1972 | Shepherd et al. |
| 3,699,956 A | 10/1972 | Kitrilakis et al. |
| 3,699,964 A | 10/1972 | Ericson |
| 3,708,324 A | 1/1973 | Stebleton |
| 3,726,281 A | 4/1973 | Norton et al. |
| 3,739,783 A | 6/1973 | Broerman |
| 3,761,013 A | 9/1973 | Schuster |
| 3,762,399 A | 10/1973 | Riedell |
| 3,768,102 A | 10/1973 | Kwan-Gett et al. |
| 3,788,324 A | 1/1974 | Lim |
| 3,794,042 A | 2/1974 | De Klotz et al. |
| 3,797,478 A | 3/1974 | Walsh et al. |
| 3,838,728 A | 10/1974 | Voegele |
| 3,841,304 A | 10/1974 | Jones |
| 3,854,483 A | 12/1974 | Powers |
| 3,861,395 A | 1/1975 | Taniguchi |
| 3,875,937 A | 4/1975 | Schmitt et al. |
| 3,879,516 A | 4/1975 | Wolvek |
| 3,882,220 A | 5/1975 | Ryder |
| 3,889,685 A | 6/1975 | Miller, Jr. et al. |
| 3,894,540 A | 7/1975 | Bonner, Jr. |
| 3,898,993 A | 8/1975 | Taniguchi |
| 3,924,634 A | 12/1975 | Taylor et al. |
| 3,926,309 A | 12/1975 | Center |
| 3,926,705 A | 12/1975 | Todd |
| 3,930,580 A | 1/1976 | Bazell et al. |
| 3,934,721 A | 1/1976 | Juster et al. |
| 3,962,519 A | 6/1976 | Rusch et al. |
| 3,967,728 A | 7/1976 | Gordon et al. |
| 3,981,299 A | 9/1976 | Murray |
| 3,983,879 A | 10/1976 | Todd |
| 4,026,296 A | 5/1977 | Stoy et al. |
| 4,029,104 A | 6/1977 | Kerber |
| 4,055,682 A | 10/1977 | Merrill |
| 4,062,363 A | 12/1977 | Bonner, Jr. |
| 4,091,922 A | 5/1978 | Egler |
| 4,119,094 A | 10/1978 | Micklus et al. |
| 4,120,715 A | 10/1978 | Ockwell et al. |
| 4,133,303 A | 1/1979 | Patel |
| 4,140,127 A | 2/1979 | Cianci et al. |
| 4,149,539 A | 4/1979 | Cianci |
| 4,168,699 A | 9/1979 | Hauser |
| 4,186,745 A | 2/1980 | Lewis et al. |
| 4,187,851 A | 2/1980 | Hauser |
| 4,196,731 A | 4/1980 | Laurin et al. |
| 4,198,983 A | 4/1980 | Becker et al. |
| 4,198,984 A | 4/1980 | Taylor |
| 4,209,010 A | 6/1980 | Ward et al. |
| 4,225,371 A | 9/1980 | Taylor et al. |
| 4,230,115 A | 10/1980 | Walz, Jr. et al. |
| 4,246,909 A | 1/1981 | Wu et al. |
| 4,249,535 A | 2/1981 | Hargest, III |
| 4,252,760 A | 2/1981 | Foster et al. |
| 4,265,848 A | 5/1981 | Rusch et al. |
| 4,266,999 A | 5/1981 | Baier |
| 4,269,310 A | 5/1981 | Uson et al. |
| 4,284,459 A | 8/1981 | Patel et al. |
| 4,287,227 A | 9/1981 | Kamada et al. |
| 4,311,146 A | 1/1982 | Wonder |
| 4,311,659 A | 1/1982 | Rey et al. |
| 4,318,406 A | 3/1982 | McLeod |
| 4,318,947 A | 3/1982 | Joung |
| 4,341,817 A | 7/1982 | Tozier et al. |
| 4,343,788 A | 8/1982 | Mustacich et al. |
| 4,366,901 A | 1/1983 | Short |
| 4,367,732 A | 1/1983 | Poulsen et al. |
| 4,378,018 A | 3/1983 | Alexander et al. |
| 4,378,796 A | 4/1983 | Milhaud |
| 4,379,506 A | 4/1983 | Davidson |
| 4,381,008 A | 4/1983 | Thomas et al. |
| 4,381,380 A | 4/1983 | LeVeen et al. |
| 4,395,806 A | 8/1983 | Wonder et al. |
| 4,411,648 A | 10/1983 | Davis et al. |
| 4,419,097 A | 12/1983 | Rowland |
| 4,428,365 A | 1/1984 | Hakky |
| 4,457,299 A | 7/1984 | Cornwell |

(56) References Cited

U.S. PATENT DOCUMENTS

| | | |
|---|---|---|
| 4,472,226 A | 9/1984 | Redinger et al. |
| 4,475,910 A | 10/1984 | Conway et al. |
| 4,477,325 A | 10/1984 | Osburn |
| 4,479,795 A | 10/1984 | Mustacich et al. |
| 4,486,504 A | 12/1984 | Chung |
| 4,515,593 A | 5/1985 | Norton |
| 4,534,768 A | 8/1985 | Osburn et al. |
| 4,539,234 A | 9/1985 | Sakamoto et al. |
| 4,540,409 A | 9/1985 | Nystrom et al. |
| 4,552,269 A | 11/1985 | Chang |
| 4,553,533 A | 11/1985 | Leighton |
| 4,563,184 A | 1/1986 | Korol |
| 4,568,340 A | 2/1986 | Giacalone |
| 4,571,239 A | 2/1986 | Heyman |
| 4,571,240 A | 2/1986 | Samson et al. |
| 4,576,599 A | 3/1986 | Lipner |
| 4,581,026 A | 4/1986 | Schneider |
| 4,581,028 A | 4/1986 | Fox, Jr. et al. |
| 4,582,762 A | 4/1986 | Onohara et al. |
| 4,586,974 A | 5/1986 | Nystrom et al. |
| 4,589,874 A | 5/1986 | Riedel et al. |
| 4,592,920 A | 6/1986 | Murtfeldt |
| 4,597,765 A | 7/1986 | Klatt |
| 4,597,931 A | 7/1986 | Watanabe et al. |
| 4,601,713 A | 7/1986 | Fuqua |
| 4,603,152 A | 7/1986 | Laurin et al. |
| 4,612,337 A | 9/1986 | Fox, Jr. et al. |
| 4,613,324 A | 9/1986 | Ghajar |
| 4,615,692 A | 10/1986 | Giacalone et al. |
| 4,615,697 A | 10/1986 | Robinson |
| 4,622,033 A | 11/1986 | Taniguchi |
| 4,623,329 A | 11/1986 | Drobish et al. |
| 4,626,250 A | 12/1986 | Schneider |
| 4,627,844 A | 12/1986 | Schmitt |
| 4,634,433 A | 1/1987 | Osborne |
| 4,637,907 A | 1/1987 | Hegel et al. |
| 4,638,790 A | 1/1987 | Conway et al. |
| 4,639,246 A * | 1/1987 | Dudley ............... A61M 25/007 128/207.14 |
| 4,640,688 A | 2/1987 | Hauser |
| 4,652,259 A | 3/1987 | O'Neil |
| 4,664,657 A | 5/1987 | Williamitis et al. |
| 4,673,401 A | 6/1987 | Jensen et al. |
| 4,677,143 A | 6/1987 | Laurin et al. |
| 4,685,913 A | 8/1987 | Austin |
| 4,686,124 A | 8/1987 | Onohara et al. |
| 4,687,470 A | 8/1987 | Okada |
| 4,692,152 A | 9/1987 | Emde |
| 4,699,616 A | 10/1987 | Nowak et al. |
| 4,710,169 A | 12/1987 | Christopher |
| 4,710,181 A | 12/1987 | Fuqua |
| 4,731,064 A | 3/1988 | Heyden |
| 4,737,219 A | 4/1988 | Taller et al. |
| 4,739,768 A | 4/1988 | Engelson |
| 4,747,845 A | 5/1988 | Korol |
| 4,754,877 A | 7/1988 | Johansson et al. |
| 4,759,753 A | 7/1988 | Schneider et al. |
| 4,769,013 A | 9/1988 | Lorenz et al. |
| 4,769,099 A | 9/1988 | Therriault et al. |
| 4,772,473 A | 9/1988 | Patel et al. |
| 4,773,901 A | 9/1988 | Norton |
| 4,775,371 A | 10/1988 | Mueller, Jr. |
| 4,790,834 A | 12/1988 | Austin |
| 4,790,835 A | 12/1988 | Elias |
| D299,865 S | 2/1989 | Kamstrup-Larsen et al. |
| 4,810,247 A | 3/1989 | Glassman |
| 4,811,847 A | 3/1989 | Reif et al. |
| 4,813,935 A | 3/1989 | Haber et al. |
| 4,820,270 A | 4/1989 | Hardcastle et al. |
| 4,820,289 A | 4/1989 | Coury et al. |
| 4,820,291 A | 4/1989 | Terauchi et al. |
| 4,820,292 A | 4/1989 | Korol et al. |
| 4,834,721 A | 5/1989 | Onohara et al. |
| 4,838,876 A | 6/1989 | Wong et al. |
| 4,846,784 A | 7/1989 | Haber |
| 4,846,909 A | 7/1989 | Klug et al. |
| 4,850,969 A | 7/1989 | Jackson |
| 4,861,337 A | 8/1989 | George |
| 4,863,424 A | 9/1989 | Blake, III et al. |
| 4,863,444 A | 9/1989 | Blomer |
| 4,863,449 A | 9/1989 | Therriault et al. |
| 4,867,748 A | 9/1989 | Samuelsen |
| 4,874,373 A | 10/1989 | Luther et al. |
| 4,876,109 A | 10/1989 | Mayer et al. |
| 4,885,049 A | 12/1989 | Johannesson |
| 4,894,059 A | 1/1990 | Larsen et al. |
| 4,902,503 A | 2/1990 | Umemura et al. |
| 4,904,260 A | 2/1990 | Ray et al. |
| 4,917,113 A | 4/1990 | Conway et al. |
| 4,917,686 A | 4/1990 | Bayston et al. |
| RE33,206 E | 5/1990 | Conway et al. |
| 4,923,450 A | 5/1990 | Maeda et al. |
| 4,925,668 A | 5/1990 | Khan et al. |
| 4,930,522 A | 6/1990 | Busnel et al. |
| 4,931,056 A | 6/1990 | Ghajar et al. |
| 4,932,938 A | 6/1990 | Goldberg et al. |
| 4,932,948 A | 6/1990 | Kernes et al. |
| 4,934,999 A | 6/1990 | Bader |
| 4,935,260 A | 6/1990 | Shlenker |
| 4,950,256 A | 8/1990 | Luther et al. |
| 4,963,137 A | 10/1990 | Heyden |
| 4,968,294 A | 11/1990 | Salama |
| 4,968,507 A | 11/1990 | Zentner et al. |
| 4,976,703 A | 12/1990 | Franetzki et al. |
| 4,981,471 A | 1/1991 | Quinn et al. |
| 4,994,047 A | 2/1991 | Walker et al. |
| 5,004,454 A | 4/1991 | Beyar et al. |
| 5,007,897 A | 4/1991 | Kalb et al. |
| 5,013,306 A | 5/1991 | Solomon et al. |
| 5,013,717 A | 5/1991 | Solomon et al. |
| 5,019,096 A | 5/1991 | Fox, Jr. et al. |
| 5,019,378 A | 5/1991 | Allen |
| 5,019,601 A | 5/1991 | Allen |
| 5,059,190 A | 10/1991 | Novak |
| 5,071,406 A | 12/1991 | Jang |
| 5,078,707 A | 1/1992 | Peter Klug |
| 5,082,006 A | 1/1992 | Jonasson |
| 5,084,037 A | 1/1992 | Barnett |
| 5,087,252 A | 2/1992 | Denard |
| 5,088,980 A | 2/1992 | Leighton |
| 5,089,205 A | 2/1992 | Huang et al. |
| 5,090,424 A | 2/1992 | Simon et al. |
| 5,098,379 A | 3/1992 | Conway et al. |
| 5,102,401 A | 4/1992 | Lambert et al. |
| 5,102,405 A | 4/1992 | Conway et al. |
| 5,109,378 A | 4/1992 | Proctor et al. |
| 5,109,601 A | 5/1992 | McBride |
| 5,112,306 A | 5/1992 | Burton et al. |
| 5,114,398 A | 5/1992 | Trick et al. |
| 5,128,088 A | 7/1992 | Shimomura et al. |
| 5,131,906 A | 7/1992 | Chen |
| 5,137,671 A | 8/1992 | Conway et al. |
| 5,140,999 A | 8/1992 | Ardito |
| 5,147,341 A | 9/1992 | Starke et al. |
| 5,165,952 A | 11/1992 | Solomon et al. |
| 5,176,666 A | 1/1993 | Conway et al. |
| 5,197,957 A | 3/1993 | Wendler |
| 5,201,724 A | 4/1993 | Hukins et al. |
| 5,209,726 A | 5/1993 | Goosen |
| 5,211,640 A | 5/1993 | Wendler |
| 5,226,530 A | 7/1993 | Golden |
| 5,234,411 A | 8/1993 | Vaillancourt |
| 5,236,422 A | 8/1993 | Eplett, Jr. |
| 5,242,391 A | 9/1993 | Place et al. |
| 5,242,428 A | 9/1993 | Palestrant |
| 5,261,896 A | 11/1993 | Conway et al. |
| 5,263,947 A | 11/1993 | Kay |
| 5,269,755 A | 12/1993 | Bodicky |
| 5,269,770 A | 12/1993 | Conway et al. |
| 5,270,358 A | 12/1993 | Asmus |
| 5,290,306 A | 3/1994 | Trotta et al. |
| 5,306,226 A | 4/1994 | Salaam |
| 5,334,175 A | 8/1994 | Conway et al. |
| 5,336,211 A | 8/1994 | Metz |

(56) References Cited

U.S. PATENT DOCUMENTS

| | | |
|---|---|---|
| 5,346,483 A | 9/1994 | Thaxton, Sr. |
| 5,348,536 A | 9/1994 | Young et al. |
| 5,352,182 A | 10/1994 | Kalb et al. |
| 5,360,402 A | 11/1994 | Conway et al. |
| 5,360,414 A * | 11/1994 | Yarger .............. A61M 25/0043 604/264 |
| 5,366,449 A | 11/1994 | Gilberg |
| 5,368,575 A | 11/1994 | Chang |
| 5,370,899 A | 12/1994 | Conway et al. |
| 5,376,085 A | 12/1994 | Conway et al. |
| 5,380,312 A | 1/1995 | Goulter |
| 5,395,333 A | 3/1995 | Brill |
| 5,409,495 A | 4/1995 | Osborn |
| 5,415,635 A | 5/1995 | Bagaoisan et al. |
| 5,417,226 A | 5/1995 | Juma |
| 5,417,666 A | 5/1995 | Coulter |
| 5,423,784 A | 6/1995 | Metz |
| 5,433,705 A | 7/1995 | Giebel et al. |
| 5,433,713 A | 7/1995 | Trotta |
| 5,447,231 A | 9/1995 | Kastenhofer |
| 5,451,424 A | 9/1995 | Solomon et al. |
| 5,454,798 A | 10/1995 | Kubalak et al. |
| 5,464,650 A | 11/1995 | Berg et al. |
| 5,479,945 A | 1/1996 | Simon |
| 5,482,740 A | 1/1996 | Conway et al. |
| 5,483,976 A | 1/1996 | McLaughlin et al. |
| 5,497,601 A | 3/1996 | Gonzalez |
| 5,501,669 A | 3/1996 | Conway et al. |
| 5,509,427 A | 4/1996 | Simon et al. |
| 5,509,899 A * | 4/1996 | Fan .................. A61L 29/06 604/103.14 |
| 5,513,659 A | 5/1996 | Buuck et al. |
| 5,513,660 A | 5/1996 | Simon et al. |
| 5,531,715 A | 7/1996 | Engelson et al. |
| 5,531,717 A | 7/1996 | Roberto et al. |
| 5,538,584 A | 7/1996 | Metz |
| 5,554,141 A | 9/1996 | Wendler |
| 5,562,599 A | 10/1996 | Beyschlag |
| 5,567,495 A | 10/1996 | Modak et al. |
| 5,569,219 A | 10/1996 | Hakki et al. |
| 5,582,599 A | 12/1996 | Daneshvar |
| 5,593,718 A | 1/1997 | Conway et al. |
| 5,599,321 A | 2/1997 | Conway et al. |
| 5,614,143 A | 3/1997 | Hager |
| 5,624,395 A | 4/1997 | Mikhail et al. |
| 5,630,429 A | 5/1997 | Dann |
| 5,643,235 A | 7/1997 | Figuerido |
| 5,670,111 A | 9/1997 | Conway et al. |
| 5,671,755 A | 9/1997 | Simon et al. |
| 5,695,485 A | 12/1997 | Duperret et al. |
| 5,702,381 A | 12/1997 | Cottenden |
| 5,707,357 A | 1/1998 | Mikhail et al. |
| 5,709,672 A | 1/1998 | Illner |
| 5,711,841 A | 1/1998 | Jaker |
| 5,724,994 A | 3/1998 | Simon et al. |
| 5,730,733 A | 3/1998 | Mortier et al. |
| 5,736,152 A | 4/1998 | Dunn |
| 5,752,525 A | 5/1998 | Simon et al. |
| 5,756,144 A | 5/1998 | Wolff et al. |
| 5,762,996 A | 6/1998 | Lucas et al. |
| 5,779,670 A | 7/1998 | Bidwell et al. |
| 5,789,018 A | 8/1998 | Engelson et al. |
| 5,795,332 A | 8/1998 | Lucas et al. |
| 5,795,334 A | 8/1998 | Cochrane, III |
| 5,795,524 A | 8/1998 | Basso, Jr. et al. |
| 5,806,527 A | 9/1998 | Borodulin et al. |
| 5,810,789 A | 9/1998 | Powers et al. |
| 5,820,607 A | 10/1998 | Tcholakian et al. |
| 5,827,247 A | 10/1998 | Kay |
| 5,827,249 A | 10/1998 | Jensen |
| 5,830,932 A | 11/1998 | Kay |
| 5,853,518 A | 12/1998 | Utas et al. |
| 5,877,243 A | 3/1999 | Sarangapani |
| 5,895,374 A | 4/1999 | Rodsten et al. |
| 5,897,535 A | 4/1999 | Feliziani et al. |
| 5,902,631 A | 5/1999 | Wang et al. |
| 5,906,575 A | 5/1999 | Conway et al. |
| 5,919,170 A | 7/1999 | Woessner |
| 5,971,954 A | 10/1999 | Conway et al. |
| 5,980,483 A | 11/1999 | Dimitri et al. |
| 5,980,507 A | 11/1999 | Fassuliotis et al. |
| 5,997,517 A | 12/1999 | Whitbourne |
| 6,004,305 A | 12/1999 | Hursman et al. |
| 6,007,524 A | 12/1999 | Schneider |
| 6,007,526 A | 12/1999 | Passalaqua et al. |
| 6,050,934 A | 4/2000 | Mikhail et al. |
| 6,053,905 A | 4/2000 | Daignault, Jr. et al. |
| 6,059,107 A | 5/2000 | Nosted et al. |
| 6,063,063 A | 5/2000 | Harboe et al. |
| 6,065,597 A | 5/2000 | Pettersson et al. |
| 6,090,075 A | 7/2000 | House |
| 6,097,976 A | 8/2000 | Yang et al. |
| 6,102,929 A | 8/2000 | Conway et al. |
| 6,113,582 A | 9/2000 | Dwork |
| 6,119,697 A | 9/2000 | Engel et al. |
| 6,131,575 A | 10/2000 | Lenker et al. |
| 6,132,399 A | 10/2000 | Shultz |
| 6,186,990 B1 | 2/2001 | Chen et al. |
| 6,206,885 B1 | 3/2001 | Ghahremani et al. |
| 6,231,501 B1 | 5/2001 | Diller |
| 6,254,570 B1 | 7/2001 | Rutner et al. |
| 6,256,525 B1 | 7/2001 | Yang et al. |
| 6,261,255 B1 | 7/2001 | Mullis et al. |
| 6,261,271 B1 | 7/2001 | Solomon et al. |
| 6,280,425 B1 | 8/2001 | Del Guercio |
| 6,299,598 B1 | 10/2001 | Bander |
| 6,306,176 B1 | 10/2001 | Whitbourne |
| 6,315,711 B1 | 11/2001 | Conway et al. |
| 6,340,465 B1 | 1/2002 | Hsu et al. |
| 6,355,004 B1 | 3/2002 | Pedersen et al. |
| 6,379,334 B1 | 4/2002 | Frassica |
| 6,383,434 B2 | 5/2002 | Conway et al. |
| 6,387,080 B1 | 5/2002 | Rødsten |
| 6,391,010 B1 | 5/2002 | Wilcox |
| 6,402,726 B1 | 6/2002 | Genese |
| 6,409,717 B1 | 6/2002 | Israelsson et al. |
| 6,437,038 B1 | 8/2002 | Chen |
| 6,440,060 B1 | 8/2002 | Latour, Jr. |
| 6,458,867 B1 * | 10/2002 | Wang .................... A61L 29/085 523/105 |
| 6,468,245 B2 | 10/2002 | Alexandersen et al. |
| 6,479,000 B2 | 11/2002 | Conway et al. |
| 6,479,726 B1 | 11/2002 | Cole |
| 6,509,319 B1 | 1/2003 | Raad et al. |
| 6,551,293 B1 | 4/2003 | Mitchell |
| 6,558,369 B2 | 5/2003 | Rosenblum |
| 6,558,792 B1 | 5/2003 | Vaabengaard et al. |
| 6,558,798 B2 | 5/2003 | Zhong et al. |
| 6,578,709 B1 | 6/2003 | Kavanagh et al. |
| 6,579,539 B2 | 6/2003 | Lawson et al. |
| 6,582,401 B1 | 6/2003 | Windheuser et al. |
| 6,596,401 B1 | 7/2003 | Terry et al. |
| 6,602,244 B2 | 8/2003 | Kavanagh et al. |
| 6,613,014 B1 | 9/2003 | Chi |
| 6,626,888 B1 | 9/2003 | Conway et al. |
| 6,632,204 B2 | 10/2003 | Guldfeldt et al. |
| 6,634,498 B2 | 10/2003 | Kayerod et al. |
| 6,638,269 B2 | 10/2003 | Wilcox |
| 6,659,937 B2 | 12/2003 | Polsky et al. |
| 6,682,555 B2 | 1/2004 | Cioanta et al. |
| 6,693,189 B2 | 2/2004 | Holt et al. |
| 6,695,831 B1 * | 2/2004 | Tsukada .............. A61M 25/0017 604/27 |
| 6,706,025 B2 | 3/2004 | Engelson et al. |
| 6,716,895 B1 | 4/2004 | Terry |
| 6,719,709 B2 | 4/2004 | Whalen et al. |
| 6,723,350 B2 | 4/2004 | Burrell et al. |
| 6,733,474 B2 | 5/2004 | Kusleika |
| 6,736,805 B2 | 5/2004 | Israelsson et al. |
| 6,740,273 B2 | 5/2004 | Lee |
| 6,767,551 B2 | 7/2004 | McGhee et al. |
| 6,780,504 B2 | 8/2004 | Rupprecht et al. |
| D496,266 S | 9/2004 | Nestenborg et al. |
| 6,787,156 B1 | 9/2004 | Bar-Shalom |

(56) References Cited

U.S. PATENT DOCUMENTS

| | | |
|---|---|---|
| 6,797,743 B2 | 9/2004 | McDonald et al. |
| 6,835,410 B2 | 12/2004 | Chabrecek et al. |
| 6,848,574 B1 | 2/2005 | Israelsson et al. |
| 6,849,070 B1 | 2/2005 | Hansen et al. |
| 6,852,098 B2 | 2/2005 | Byrne |
| 6,852,105 B2 | 2/2005 | Bolmsjo et al. |
| D503,335 S | 3/2005 | Risberg et al. |
| 6,869,416 B2 | 3/2005 | Windheuser et al. |
| 6,872,195 B2 | 3/2005 | Modak et al. |
| 6,887,230 B2 | 5/2005 | Kubalak et al. |
| 6,939,339 B1 | 9/2005 | Axexandersen et al. |
| 6,939,554 B2 | 9/2005 | McDonald et al. |
| 6,951,902 B2 | 10/2005 | McDonald et al. |
| 6,972,040 B2 | 12/2005 | Rioux et al. |
| 7,001,370 B2 | 2/2006 | Kubalak et al. |
| 7,033,367 B2 | 4/2006 | Ghahremani et al. |
| 7,066,912 B2 | 6/2006 | Nestenborg et al. |
| 7,087,048 B2 | 8/2006 | Israelsson et al. |
| 7,094,220 B2 | 8/2006 | Tanghoj et al. |
| 7,112,298 B2 | 9/2006 | Kampa et al. |
| 7,160,277 B2 | 1/2007 | Elson et al. |
| 7,166,092 B2 | 1/2007 | Elson et al. |
| 7,204,940 B2 | 4/2007 | McDonald et al. |
| 7,211,275 B2 | 5/2007 | Ying et al. |
| 7,294,117 B2 | 11/2007 | Provost-tine et al. |
| 7,311,698 B2 | 12/2007 | Tanghoj et al. |
| 7,329,412 B2 | 2/2008 | Modak et al. |
| 7,331,948 B2 | 2/2008 | Skarda |
| 7,334,679 B2 | 2/2008 | Givens, Jr. |
| 7,374,040 B2 | 5/2008 | Lee et al. |
| 7,380,658 B2 | 6/2008 | Murray et al. |
| 7,402,559 B2 | 7/2008 | Catania et al. |
| 7,445,812 B2 | 11/2008 | Schmidt et al. |
| 7,458,964 B2 | 12/2008 | Mosler et al. |
| 7,476,223 B2 | 1/2009 | McBride |
| 7,507,229 B2 | 3/2009 | Hewitt et al. |
| 7,517,343 B2 | 4/2009 | Tanghoj et al. |
| 7,571,804 B2 | 8/2009 | Kjellmann Bruun et al. |
| 7,601,158 B2 | 10/2009 | House |
| 7,615,045 B2 | 11/2009 | Israelsson et al. |
| 7,628,784 B2 | 12/2009 | Diaz et al. |
| 7,632,256 B2 | 12/2009 | Mosler et al. |
| D609,819 S | 2/2010 | Tomes et al. |
| 7,662,146 B2 | 2/2010 | House |
| 7,670,331 B2 | 3/2010 | Tanghoej |
| 7,682,353 B2 | 3/2010 | Tanghoj et al. |
| 7,691,476 B2 | 4/2010 | Finley |
| 7,717,902 B2 | 5/2010 | Sauer |
| 7,749,529 B2 | 7/2010 | Ash et al. |
| 7,770,726 B2 | 8/2010 | Murray et al. |
| 7,770,728 B2 | 8/2010 | Kærn |
| 7,780,642 B2 | 8/2010 | Rasmussen et al. |
| 7,789,873 B2 | 9/2010 | Kubalak et al. |
| 7,820,734 B2 | 10/2010 | McGhee |
| 7,823,722 B2 | 11/2010 | Bezou et al. |
| 7,846,133 B2 | 12/2010 | Windheuser et al. |
| 7,867,220 B2 | 1/2011 | Tanghoj |
| 7,886,907 B2 | 2/2011 | Murray et al. |
| 7,918,831 B2 | 4/2011 | House |
| 7,938,838 B2 | 5/2011 | House |
| 7,947,021 B2 | 5/2011 | Bourne et al. |
| 7,985,217 B2 | 7/2011 | Mosler et al. |
| 8,007,464 B2 | 8/2011 | Gellman |
| 8,011,505 B2 | 9/2011 | Murray et al. |
| 8,051,981 B2 | 11/2011 | Murray et al. |
| 8,052,673 B2 | 11/2011 | Nestenborg |
| 8,053,030 B2 | 11/2011 | Gilman |
| 8,066,693 B2 | 11/2011 | Tanghoj et al. |
| 8,127,922 B2 | 3/2012 | Nordholm et al. |
| 8,133,580 B2 | 3/2012 | Dias et al. |
| 8,163,327 B2 | 4/2012 | Finley |
| 8,177,774 B2 | 5/2012 | House |
| 8,181,778 B1 | 5/2012 | Van Groningen et al. |
| 8,192,413 B2 | 6/2012 | Bjerregaard |
| 8,201,689 B2 | 6/2012 | Kaern |
| 8,205,745 B2 | 6/2012 | Murray et al. |
| 8,207,393 B2 | 6/2012 | Bach |
| 8,230,993 B2 | 7/2012 | Tanghoej |
| 8,267,919 B2 | 9/2012 | Utas et al. |
| 8,282,624 B2 | 10/2012 | Tanghoej et al. |
| 8,287,519 B2 | 10/2012 | Smith |
| 8,287,890 B2 | 10/2012 | Elton |
| 8,298,202 B2 | 10/2012 | McCray |
| 8,303,556 B2 | 11/2012 | White |
| 8,317,775 B2 | 11/2012 | House |
| 8,328,792 B2 | 12/2012 | Nishtala et al. |
| 8,356,457 B2 | 1/2013 | Murray et al. |
| 8,377,498 B2 | 2/2013 | Rindlav-Westling et al. |
| 8,377,559 B2 | 2/2013 | Gilman |
| 8,382,708 B2 | 2/2013 | Mayback et al. |
| 8,409,171 B2 | 4/2013 | Hannon et al. |
| 8,454,569 B2 | 6/2013 | Kull-Osterlin et al. |
| 8,459,455 B2 | 6/2013 | Frojd |
| 8,475,434 B2 | 7/2013 | Frojd |
| 8,523,843 B2 | 9/2013 | Kavanagh et al. |
| 8,556,884 B2 | 10/2013 | Hong et al. |
| 8,720,685 B2 | 5/2014 | Murray et al. |
| 8,805,533 B2 | 8/2014 | Boggs, II et al. |
| 8,871,869 B2 | 10/2014 | Dias et al. |
| 8,888,747 B2 | 11/2014 | House |
| 8,919,553 B2 | 12/2014 | Murray et al. |
| 8,974,438 B2 | 3/2015 | Hong et al. |
| 9,072,862 B2 | 7/2015 | Murray et al. |
| 9,108,020 B1 | 8/2015 | Feloney |
| 9,138,510 B2 | 9/2015 | Madsen |
| 9,144,659 B2 | 9/2015 | Tanghoj |
| 9,168,354 B2 | 10/2015 | Hannon et al. |
| 9,186,438 B2 | 11/2015 | Gravesen et al. |
| 9,192,506 B2 | 11/2015 | Tanghoej et al. |
| 9,192,740 B2 | 11/2015 | Frojd |
| 9,199,057 B2 | 12/2015 | Nielsen |
| 9,205,222 B2 | 12/2015 | Tanghoj |
| 9,289,575 B2 | 3/2016 | Dye |
| 9,314,585 B2 | 4/2016 | Nestenborg et al. |
| 2001/0001443 A1 | 5/2001 | Kayerod et al. |
| 2001/0031933 A1 | 10/2001 | Cannon |
| 2001/0054562 A1 | 12/2001 | Pettersson et al. |
| 2002/0032406 A1 | 3/2002 | Kusleika |
| 2002/0103467 A1 | 8/2002 | Kubalak |
| 2002/0132049 A1 | 9/2002 | Leonard et al. |
| 2002/0169438 A1 | 11/2002 | Sauer |
| 2002/0182265 A1 | 12/2002 | Burrell et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018322 A1 | 1/2003 | Tanghoj et al. |
| 2003/0055403 A1 | 3/2003 | Nestenborg et al. |
| 2003/0060807 A1 | 3/2003 | Tanghoj et al. |
| 2003/0083644 A1 | 5/2003 | Avaltroni |
| 2003/0130646 A1 | 7/2003 | Kubalak et al. |
| 2003/0168365 A1 | 9/2003 | Kaern |
| 2004/0030301 A1 | 2/2004 | Hunter |
| 2004/0074794 A1 | 4/2004 | Conway et al. |
| 2004/0097892 A1 | 5/2004 | Evans et al. |
| 2004/0133156 A1 | 7/2004 | Diaz et al. |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0193143 A1 | 9/2004 | Sauer |
| 2004/0234572 A1 | 11/2004 | Martinod et al. |
| 2004/0236293 A1 | 11/2004 | Tanghoj et al. |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0015076 A1 | 1/2005 | Giebmeyer et al. |
| 2005/0031872 A1 | 2/2005 | Schmidt et al. |
| 2005/0043715 A1 | 2/2005 | Nestenborg et al. |
| 2005/0049577 A1 | 3/2005 | Snell et al. |
| 2005/0070882 A1 | 3/2005 | McBride |
| 2005/0080399 A1 | 4/2005 | Bolmsjo et al. |
| 2005/0101924 A1 | 5/2005 | Elson et al. |
| 2005/0109648 A1 | 5/2005 | Kerzman et al. |
| 2005/0137582 A1 | 6/2005 | Kull-Osterlin et al. |

(56) References Cited

U.S. PATENT DOCUMENTS

| | | |
|---|---|---|
| 2005/0148950 A1 | 7/2005 | Windheuser et al. |
| 2005/0177104 A1 | 8/2005 | Conway |
| 2005/0199521 A1 | 9/2005 | Givens |
| 2005/0214443 A1 | 9/2005 | Madsen |
| 2005/0282977 A1 | 12/2005 | Stempel et al. |
| 2005/0283136 A1 | 12/2005 | Skarda |
| 2006/0025753 A1 | 2/2006 | Kubalak et al. |
| 2006/0041246 A1 | 2/2006 | Provost-tine et al. |
| 2006/0058777 A1 | 3/2006 | Nielsen |
| 2006/0163097 A1 | 7/2006 | Murray et al. |
| 2006/0196783 A1 | 9/2006 | Bruun et al. |
| 2006/0229576 A1 | 10/2006 | Conway et al. |
| 2006/0240069 A1 | 10/2006 | Utas et al. |
| 2007/0005024 A1 | 1/2007 | Weber et al. |
| 2007/0016168 A1 | 1/2007 | Conway |
| 2007/0059350 A1* | 3/2007 | Kennedy ............ A61F 13/00068 424/448 |
| 2007/0088330 A1 | 4/2007 | House |
| 2007/0161971 A1 | 7/2007 | House |
| 2007/0287800 A1 | 12/2007 | Acquarulo et al. |
| 2007/0289887 A1 | 12/2007 | Murray et al. |
| 2008/0015527 A1 | 1/2008 | House |
| 2008/0091145 A1 | 4/2008 | House |
| 2008/0103464 A1 | 5/2008 | Mosler et al. |
| 2008/0125513 A1 | 5/2008 | Kristiansen |
| 2008/0172040 A1 | 7/2008 | Smith |
| 2008/0172042 A1 | 7/2008 | House |
| 2008/0177217 A1 | 7/2008 | Polaschegg |
| 2008/0179208 A1 | 7/2008 | Murray et al. |
| 2008/0183262 A1 | 7/2008 | Dowling |
| 2008/0193497 A1 | 8/2008 | Samuelsen et al. |
| 2008/0215021 A1 | 9/2008 | Cisko, Jr. et al. |
| 2008/0243081 A1 | 10/2008 | Nance et al. |
| 2008/0279907 A1 | 11/2008 | Ash et al. |
| 2008/0281291 A1 | 11/2008 | Tihon et al. |
| 2009/0000970 A1 | 1/2009 | Bordeau et al. |
| 2009/0005725 A1 | 1/2009 | Shorey |
| 2009/0012208 A1 | 1/2009 | Madsen et al. |
| 2009/0043287 A1 | 2/2009 | Mosler et al. |
| 2009/0048537 A1 | 2/2009 | Lydon et al. |
| 2009/0048570 A1 | 2/2009 | Jensen |
| 2009/0062754 A1 | 3/2009 | Tang |
| 2009/0101531 A1 | 4/2009 | Nordholm et al. |
| 2009/0131917 A1 | 5/2009 | Kavanagh et al. |
| 2009/0163884 A1 | 6/2009 | Kull-Osterlin et al. |
| 2009/0200187 A1 | 8/2009 | Nestenborg et al. |
| 2009/0208368 A1 | 8/2009 | Waldrep et al. |
| 2009/0221992 A1 | 9/2009 | Hannon et al. |
| 2010/0010086 A1 | 1/2010 | Ash et al. |
| 2010/0030197 A1 | 2/2010 | House |
| 2010/0036363 A1 | 2/2010 | Watanabe et al. |
| 2010/0086580 A1 | 4/2010 | Nyman et al. |
| 2010/0133172 A1 | 6/2010 | Song et al. |
| 2010/0155268 A1 | 6/2010 | Murray et al. |
| 2010/0256576 A1 | 10/2010 | Aggarwal et al. |
| 2011/0056852 A1 | 3/2011 | Frojd |
| 2011/0059874 A1* | 3/2011 | Rooijmans ................ C08F 2/50 508/100 |
| 2011/0060317 A1* | 3/2011 | Frojd ................ A61M 25/0009 604/544 |
| 2011/0114520 A1 | 5/2011 | Matthison-Hansen |
| 2011/0137296 A1 | 6/2011 | Tanghoj |
| 2011/0152843 A1 | 6/2011 | Wedlin et al. |
| 2011/0178507 A1 | 7/2011 | Bracken et al. |
| 2011/0184386 A1 | 7/2011 | House |
| 2011/0213025 A1 | 9/2011 | Finch, Jr. |
| 2011/0284409 A1 | 11/2011 | Murray et al. |
| 2011/0295239 A1 | 12/2011 | Gustavsson |
| 2012/0179144 A1 | 7/2012 | Carleo |
| 2012/0219742 A1 | 8/2012 | Gravesen et al. |
| 2012/0228165 A1 | 9/2012 | Murray et al. |
| 2012/0239005 A1 | 9/2012 | Conway et al. |
| 2012/0271101 A1 | 10/2012 | Tan |
| 2012/0316515 A1 | 12/2012 | Terry |
| 2013/0006226 A1 | 1/2013 | Hong et al. |
| 2013/0037306 A1 | 2/2013 | Kim |
| 2013/0085469 A1 | 4/2013 | Polaschegg |
| 2013/0131647 A1 | 5/2013 | Nielsen |
| 2013/0138083 A1 | 5/2013 | Tennican |
| 2013/0138088 A1 | 5/2013 | Nielsen |
| 2013/0146599 A1 | 6/2013 | Murray et al. |
| 2013/0153446 A1 | 6/2013 | Utas et al. |
| 2013/0161208 A1 | 6/2013 | Gustavsson |
| 2013/0161227 A1 | 6/2013 | Gustavsson |
| 2013/0186778 A1 | 7/2013 | Terry |
| 2013/0253426 A1* | 9/2013 | Campbell ............ A61M 25/10 604/103.02 |
| 2013/0261608 A1 | 10/2013 | Tanghoj |
| 2013/0264227 A1 | 10/2013 | Frojd |
| 2014/0066904 A1 | 3/2014 | Young |
| 2014/0066905 A1* | 3/2014 | Young ................ A61M 25/0113 604/544 |
| 2014/0194857 A1 | 7/2014 | Eilat |
| 2015/0001107 A1 | 1/2015 | Gustavsson |
| 2015/0051587 A1 | 2/2015 | Rolsted et al. |
| 2015/0068927 A1 | 3/2015 | McBurney et al. |
| 2015/0105756 A1 | 4/2015 | O'Brien et al. |
| 2015/0126975 A1 | 5/2015 | Wuthier |
| 2015/0133898 A1 | 5/2015 | Murray et al. |
| 2015/0202405 A1 | 7/2015 | Schertiger et al. |
| 2015/0231377 A1 | 8/2015 | Tierney et al. |
| 2015/0258305 A1 | 9/2015 | Dye |
| 2015/0265801 A1 | 9/2015 | Rostami |
| 2015/0273183 A1 | 10/2015 | Foley et al. |
| 2015/0297861 A1 | 10/2015 | Passalaqua et al. |
| 2015/0297862 A1 | 10/2015 | Sadik et al. |
| 2015/0314103 A1 | 11/2015 | Hannon et al. |
| 2015/0335854 A1 | 11/2015 | Dvarsater et al. |
| 2015/0335856 A1 | 11/2015 | Utas et al. |
| 2015/0343171 A1 | 12/2015 | Hannon |
| 2015/0352324 A1 | 12/2015 | Palmer |
| 2015/0359996 A1 | 12/2015 | Arora et al. |
| 2016/0001037 A1 | 1/2016 | Hong et al. |
| 2016/0038652 A1 | 2/2016 | Gilman |
| 2016/0038713 A1 | 2/2016 | Kearns et al. |
| 2016/0120688 A1 | 5/2016 | Lee |
| 2016/0184551 A1 | 6/2016 | Nyman et al. |
| 2016/0220784 A1 | 8/2016 | Palmer |
| 2018/0104444 A1 | 4/2018 | Yin et al. |

FOREIGN PATENT DOCUMENTS

| | | |
|---|---|---|
| CN | 1106744 A | 8/1995 |
| CN | 2907580 Y | 6/2007 |
| DE | 352014 C | 4/1922 |
| DE | 1913976 U | 4/1965 |
| DE | 4135502 C1 | 2/1993 |
| DE | 4303899 A1 | 8/1994 |
| DE | 19826746 C1 | 11/1999 |
| DE | 10213411 A1 | 10/2003 |
| DE | 10259002 A1 | 10/2003 |
| EP | 0055023 A2 | 6/1982 |
| EP | 0182409 A1 | 5/1986 |
| EP | 0184629 A2 | 6/1986 |
| EP | 0187846 A1 | 7/1986 |
| EP | 0193406 A2 | 9/1986 |
| EP | 0217771 | 4/1987 |
| EP | 0218203 A1 | 4/1987 |
| EP | 0236458 A1 | 9/1987 |
| EP | 0252918 A1 | 1/1988 |
| EP | 0298634 A1 | 1/1989 |
| EP | 0303487 A2 | 2/1989 |
| EP | 0335564 A1 | 10/1989 |
| EP | 0352043 A1 | 1/1990 |
| EP | 0390720 A1 | 10/1990 |
| EP | 0407218 A1 | 1/1991 |
| EP | 0471553 A1 | 2/1992 |
| EP | 0479935 A1 | 4/1992 |
| EP | 0528965 A1 | 3/1993 |
| EP | 0553960 A1 | 8/1993 |
| EP | 0590104 A1 | 4/1994 |
| EP | 0598191 A1 | 5/1994 |
| EP | 0663196 A1 | 7/1995 |
| EP | 0677299 | 10/1995 |

(56) References Cited

FOREIGN PATENT DOCUMENTS

| | | |
|---|---|---|
| EP | 0680895 A1 | 11/1995 |
| EP | 0685179 A1 | 12/1995 |
| EP | 0699086 A1 | 3/1996 |
| EP | 0767639 A1 | 4/1997 |
| EP | 0768069 A1 | 4/1997 |
| EP | 0795339 A1 | 9/1997 |
| EP | 0815037 A1 | 1/1998 |
| EP | 0909249 A1 | 4/1999 |
| EP | 0923398 | 6/1999 |
| EP | 0935478 A1 | 8/1999 |
| EP | 0959930 | 12/1999 |
| EP | 0977610 A2 | 2/2000 |
| EP | 1023882 | 8/2000 |
| EP | 1047360 A1 | 11/2000 |
| EP | 1090656 | 4/2001 |
| EP | 1115450 A1 | 7/2001 |
| EP | 1131022 A1 | 9/2001 |
| EP | 1145729 | 10/2001 |
| EP | 1245205 | 10/2002 |
| EP | 1308146 | 5/2003 |
| EP | 1347723 A1 | 10/2003 |
| EP | 1406690 A2 | 4/2004 |
| EP | 1427467 A2 | 6/2004 |
| EP | 1485158 A2 | 12/2004 |
| EP | 1498151 | 1/2005 |
| EP | 1578308 A1 | 9/2005 |
| EP | 1606196 A2 | 12/2005 |
| EP | 1615690 A1 | 1/2006 |
| EP | 1629799 A1 | 3/2006 |
| EP | 1641510 A1 | 4/2006 |
| EP | 1786501 A2 | 5/2007 |
| EP | 1788990 A1 | 5/2007 |
| EP | 1793938 A1 | 6/2007 |
| EP | 1799163 A1 | 6/2007 |
| EP | 1904003 A2 | 4/2008 |
| EP | 1948279 A1 | 7/2008 |
| EP | 1955683 A1 | 8/2008 |
| EP | 2275058 A1 | 1/2011 |
| EP | 2292293 A1 | 3/2011 |
| EP | 2292294 A1 | 3/2011 |
| EP | 2423125 A1 | 2/2012 |
| EP | 2423126 A1 | 2/2012 |
| EP | 2423127 A1 | 2/2012 |
| EP | 2450076 A1 | 5/2012 |
| EP | 2468347 A1 | 6/2012 |
| EP | 2644224 B1 | 11/2018 |
| FR | 1558162 A | 2/1969 |
| FR | 96086 E | 5/1972 |
| FR | 2351634 A1 | 12/1977 |
| FR | 2731345 A1 | 9/1996 |
| FR | 2794638 A1 | 12/2000 |
| FR | 2855399 A1 | 12/2004 |
| GB | 322426 A | 12/1929 |
| GB | 1131865 A | 10/1968 |
| GB | 2106784 A | 4/1983 |
| GB | 2150938 A | 7/1985 |
| GB | 2187670 A | 9/1987 |
| GB | 2231801 A | 11/1990 |
| GB | 2239804 A | 7/1991 |
| GB | 2284764 | 6/1995 |
| GB | 2462267 A | 2/2010 |
| JP | S59-218157 A | 12/1984 |
| JP | S59-228856 A | 12/1984 |
| JP | S59218157 A | 12/1984 |
| JP | H02-18157 A | 1/1990 |
| JP | H10-277144 A | 10/1998 |
| JP | 2001-50329 A | 2/2001 |
| JP | 2002-543885 A | 12/2002 |
| JP | 2007167158 A | 7/2007 |
| JP | 2008-51549 A | 3/2008 |
| JP | 2008-508077 A | 3/2008 |
| JP | 2008-526377 A | 7/2008 |
| JP | 2009-125583 A | 6/2009 |
| JP | 2010-538106 A | 12/2010 |
| WO | 1984001102 A1 | 3/1984 |
| WO | 1986000816 A1 | 2/1986 |
| WO | 1986006284 | 11/1986 |
| WO | 1987001582 A1 | 3/1987 |
| WO | 1989003232 A1 | 4/1989 |
| WO | 1989009626 A1 | 10/1989 |
| WO | 1990004431 A1 | 5/1990 |
| WO | 1991010466 A1 | 7/1991 |
| WO | 1991017728 A1 | 11/1991 |
| WO | 92/08426 A1 | 5/1992 |
| WO | 1992008426 A1 | 5/1992 |
| WO | 1992010220 A1 | 6/1992 |
| WO | 1992011826 A1 | 7/1992 |
| WO | 1992019192 A1 | 11/1992 |
| WO | 1993000054 A1 | 1/1993 |
| WO | 1993011821 A1 | 6/1993 |
| WO | 1993014806 A1 | 8/1993 |
| WO | 1994006377 A1 | 3/1994 |
| WO | 1994016747 A1 | 8/1994 |
| WO | 1994026215 A1 | 11/1994 |
| WO | 1995008968 A1 | 4/1995 |
| WO | 1995009667 A1 | 4/1995 |
| WO | 1995017862 A1 | 7/1995 |
| WO | 1995034253 A1 | 12/1995 |
| WO | 1996000541 A1 | 1/1996 |
| WO | 1996004119 A1 | 2/1996 |
| WO | 9607447 A1 | 3/1996 |
| WO | 1996019254 A1 | 6/1996 |
| WO | 1996026688 A1 | 9/1996 |
| WO | 1996030277 A1 | 10/1996 |
| WO | 1996034587 A1 | 11/1996 |
| WO | 9641653 A1 | 12/1996 |
| WO | 1996038192 A1 | 12/1996 |
| WO | 1996039096 A1 | 12/1996 |
| WO | 1997025947 A1 | 7/1997 |
| WO | 1997026937 | 7/1997 |
| WO | 1997041811 | 11/1997 |
| WO | 1998006642 A1 | 2/1998 |
| WO | 1999007313 A1 | 2/1999 |
| WO | 1999030761 A1 | 6/1999 |
| WO | 1999036009 A1 | 7/1999 |
| WO | 2000025848 A2 | 5/2000 |
| WO | 0030696 A1 | 6/2000 |
| WO | 2000030575 A1 | 6/2000 |
| WO | 2000047494 | 8/2000 |
| WO | 2001043807 | 6/2001 |
| WO | 2001052763 | 7/2001 |
| WO | 2001093935 | 12/2001 |
| WO | 2002036192 | 5/2002 |
| WO | 2002053070 A1 | 7/2002 |
| WO | 2002060361 A2 | 8/2002 |
| WO | 2003002178 | 1/2003 |
| WO | 2003008029 A2 | 1/2003 |
| WO | 2003022333 A1 | 3/2003 |
| WO | 2003064279 A1 | 8/2003 |
| WO | 03/093357 A1 | 11/2003 |
| WO | 2003092779 | 11/2003 |
| WO | 2004004611 A1 | 1/2004 |
| WO | 2004004796 A1 | 1/2004 |
| WO | 2004030722 | 4/2004 |
| WO | 2004032992 A2 | 4/2004 |
| WO | 2004045696 A1 | 6/2004 |
| WO | 2004050155 | 6/2004 |
| WO | 2004052440 | 6/2004 |
| WO | 2004056290 A1 | 7/2004 |
| WO | 2004056414 | 7/2004 |
| WO | 2004056909 A1 | 7/2004 |
| WO | 2004075944 | 9/2004 |
| WO | 2004089454 | 10/2004 |
| WO | 2005004964 | 1/2005 |
| WO | 2005014055 A2 | 2/2005 |
| WO | 2005061035 | 7/2005 |
| WO | 2005092418 | 10/2005 |
| WO | 2006005349 A2 | 1/2006 |
| WO | 2006009509 A1 | 1/2006 |
| WO | 2006009596 A1 | 1/2006 |
| WO | 2006017439 A2 | 2/2006 |
| WO | 2006021590 A1 | 3/2006 |
| WO | 2006027349 A1 | 3/2006 |
| WO | 2006037321 A1 | 4/2006 |

(56) References Cited

FOREIGN PATENT DOCUMENTS

| | | |
|---|---|---|
| WO | 2006097109 A2 | 9/2006 |
| WO | 2006110695 A2 | 10/2006 |
| WO | 2006112782 A1 | 10/2006 |
| WO | 2006130776 A2 | 12/2006 |
| WO | 2007001526 A2 | 1/2007 |
| WO | 2007038988 A1 | 4/2007 |
| WO | 2007083033 A2 | 7/2007 |
| WO | 2008089770 A1 | 7/2008 |
| WO | 2008104603 A1 | 9/2008 |
| WO | 2008138351 A1 | 11/2008 |
| WO | 2008138352 A1 | 11/2008 |
| WO | 2008151074 A1 | 12/2008 |
| WO | 2009000277 A1 | 12/2008 |
| WO | 2009012336 A1 | 1/2009 |
| WO | 2009043872 A1 | 4/2009 |
| WO | 2009068043 A2 | 6/2009 |
| WO | 2009080265 A1 | 7/2009 |
| WO | 2009108243 A1 | 9/2009 |
| WO | 2010006620 A1 | 1/2010 |
| WO | 2010041084 A1 | 4/2010 |
| WO | 2010054659 A1 | 5/2010 |
| WO | 2010054666 A1 | 5/2010 |
| WO | 2010129362 A1 | 11/2010 |
| WO | 2010130261 A1 | 11/2010 |
| WO | 2010149174 A1 | 12/2010 |
| WO | 2010149175 A1 | 12/2010 |
| WO | 2010151682 A2 | 12/2010 |
| WO | 2011011023 A1 | 1/2011 |
| WO | 2011014201 A1 | 2/2011 |
| WO | 2011019359 A1 | 2/2011 |
| WO | 2011026929 A1 | 3/2011 |
| WO | 2011026930 A1 | 3/2011 |
| WO | 2011063816 A1 | 6/2011 |
| WO | 2011073403 A1 | 6/2011 |
| WO | 2011076211 A1 | 6/2011 |
| WO | 2011079129 A1 | 6/2011 |
| WO | 2011109393 A1 | 9/2011 |
| WO | 2012016570 A2 | 2/2012 |
| WO | 2012016571 A2 | 2/2012 |
| WO | 2012079590 A1 | 6/2012 |
| WO | 2012085124 A1 | 6/2012 |
| WO | 2012/139214 A1 | 10/2012 |
| WO | 2012134804 A1 | 10/2012 |
| WO | 2013010745 A1 | 1/2013 |
| WO | 2013029621 A1 | 3/2013 |
| WO | 15069843 A2 | 5/2015 |
| WO | 15090338 A1 | 6/2015 |
| WO | 2015/105942 A1 | 7/2015 |
| WO | 15142506 A1 | 9/2015 |

OTHER PUBLICATIONS

Amirkhai Il et al., "Nitric Oxide Complexes of Trimethylaluminium" Journal of Organometallic Chemistry, 149 (1978).
Angus "Chemie GmbH Technical Data Sheet", AMP-95, TDS 10A (2000).
Hollister, "Vapro intermittent catheter brochure" (2009).
Johnson et al. "Activities of a Nitrofurazone-Containing Urinary Catheter and a Silver Hydrogel Catheter against Multidrug-Resistant Bacteria Characteristic of Catheter-Associated Urinary Tract Infection" Antimicrobial Agents and Chemotherapy, Dec. 1999.
Lubrizol, "Neutralizing Carbopol®* and Pemulen™* Polymers in Aqueous and Hydroalcoholic Systems" Technical Data Sheet TDS-237 Edition: Sep. 16, 2009.
Newman "Intermittent Catheterization and Current Best Practices: Catheter Design and Types"; http://www.medscape.com/viewarticle/745908_8, last accessed May 31, 2013.
EP 15836062.8 filed Feb. 17, 2017 Extended European Search Report dated Feb. 20, 2018.
JP 2017-511223 filed Feb. 24, 2017 Office Action dated Jun. 4, 2019.
U.S. Appl. No. 15/506,723, filed Feb. 24, 2017 Non-Final Office Action dated Aug. 27, 2019.

* cited by examiner

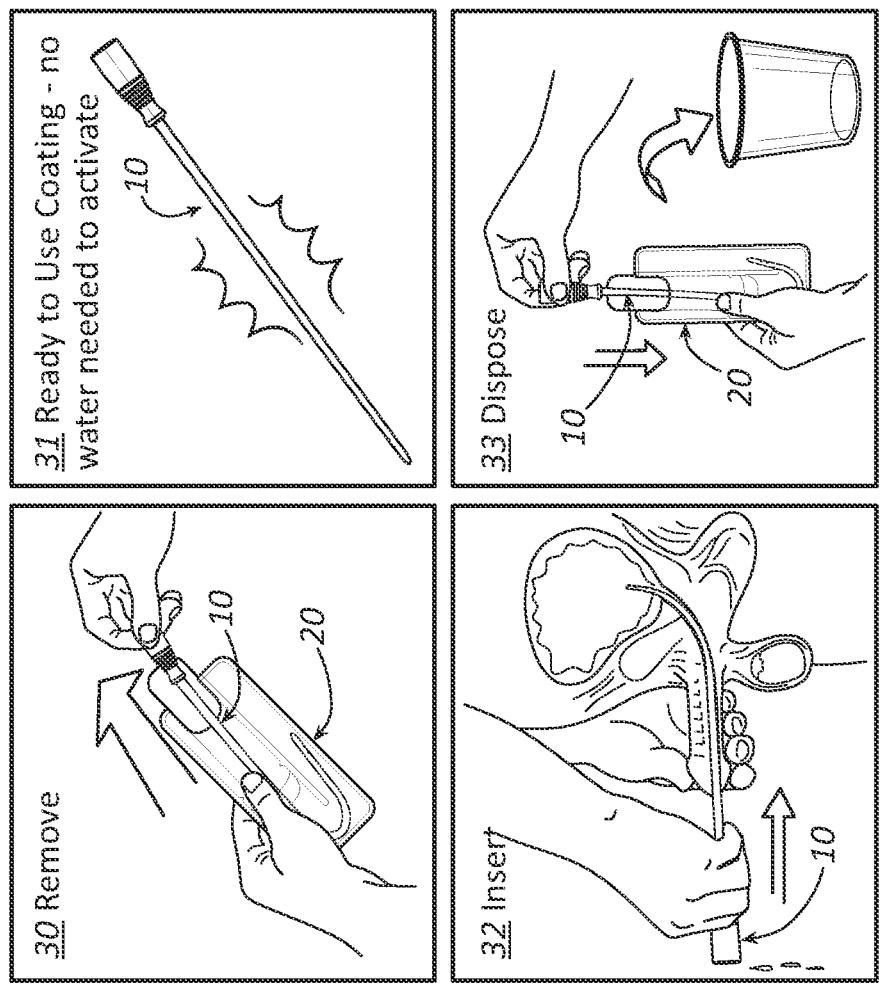
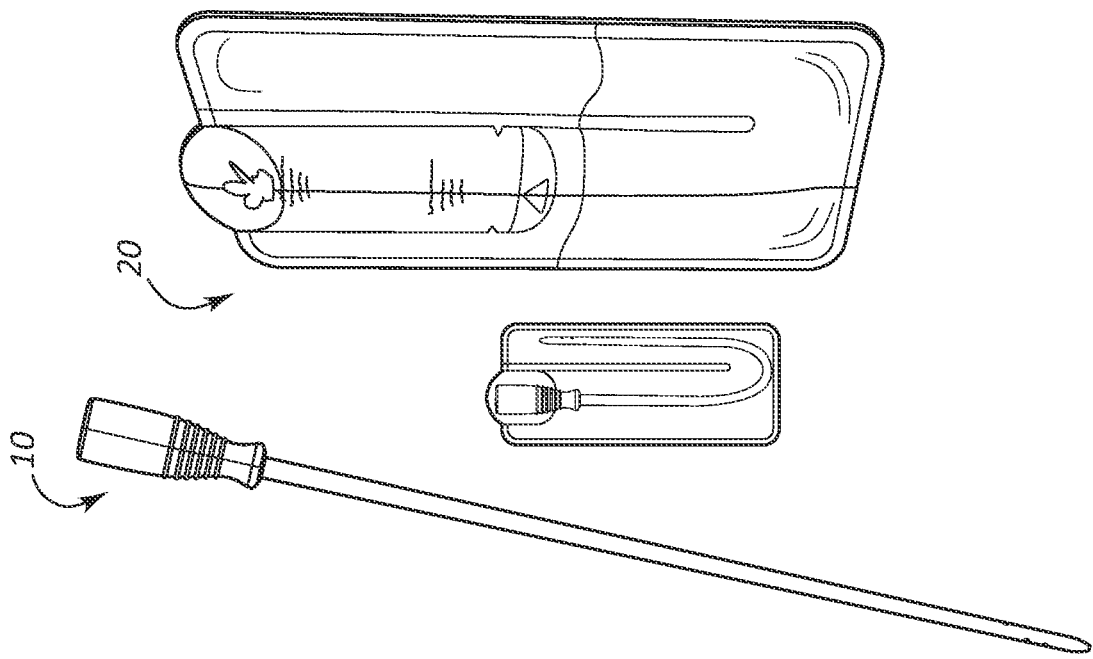
FIG. 1

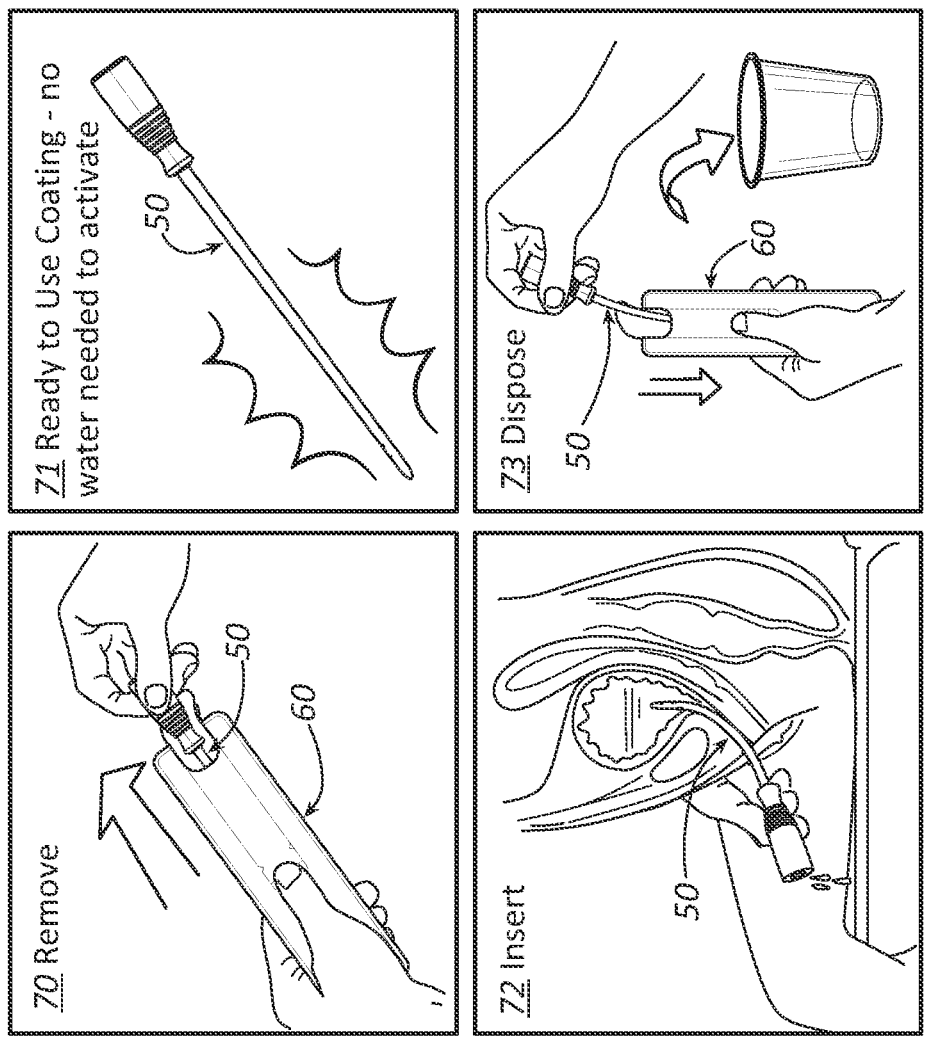
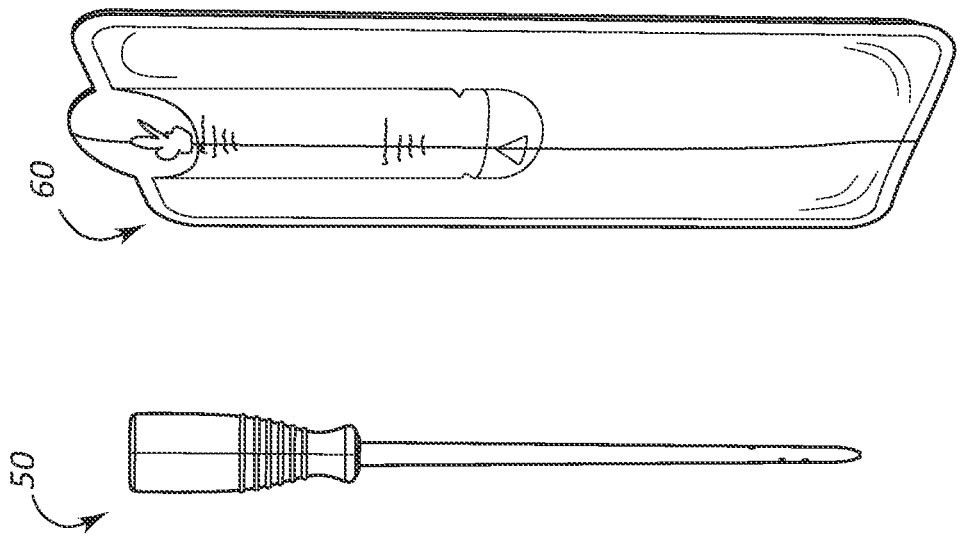
FIG. 2

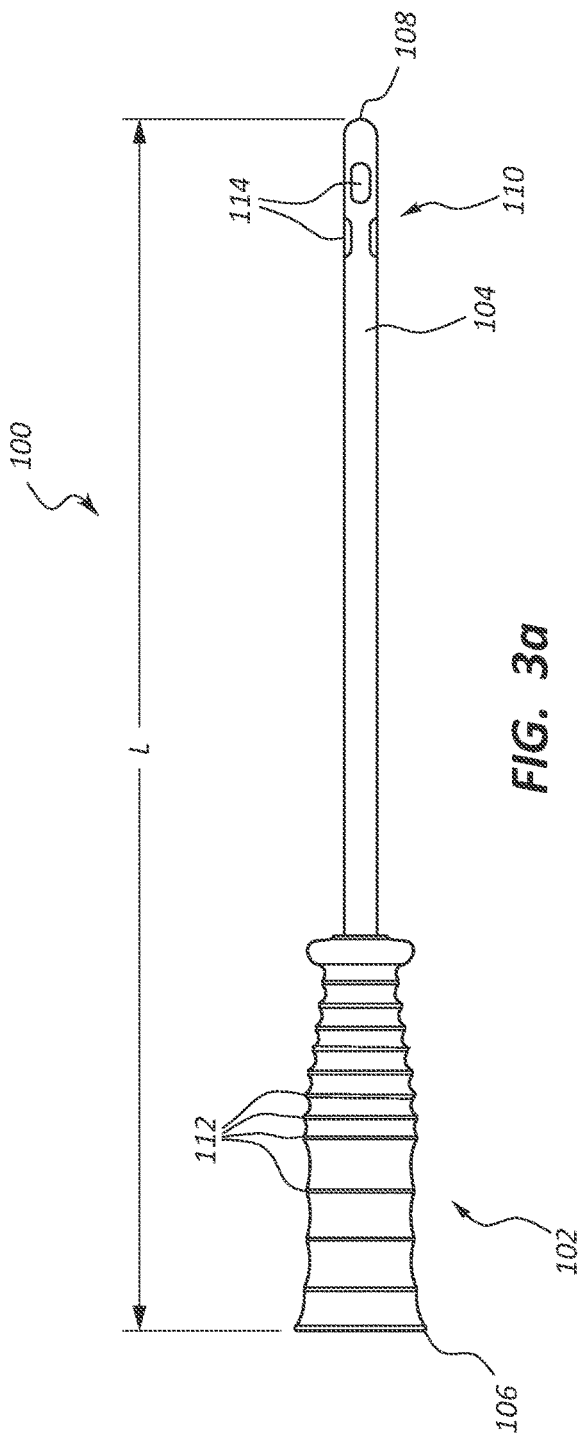
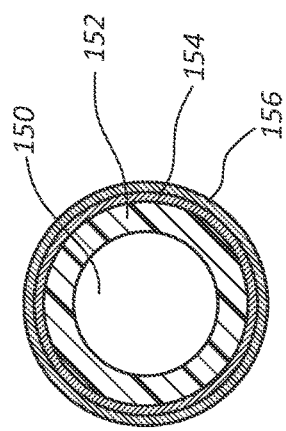
FIG. 3a
FIG. 3b

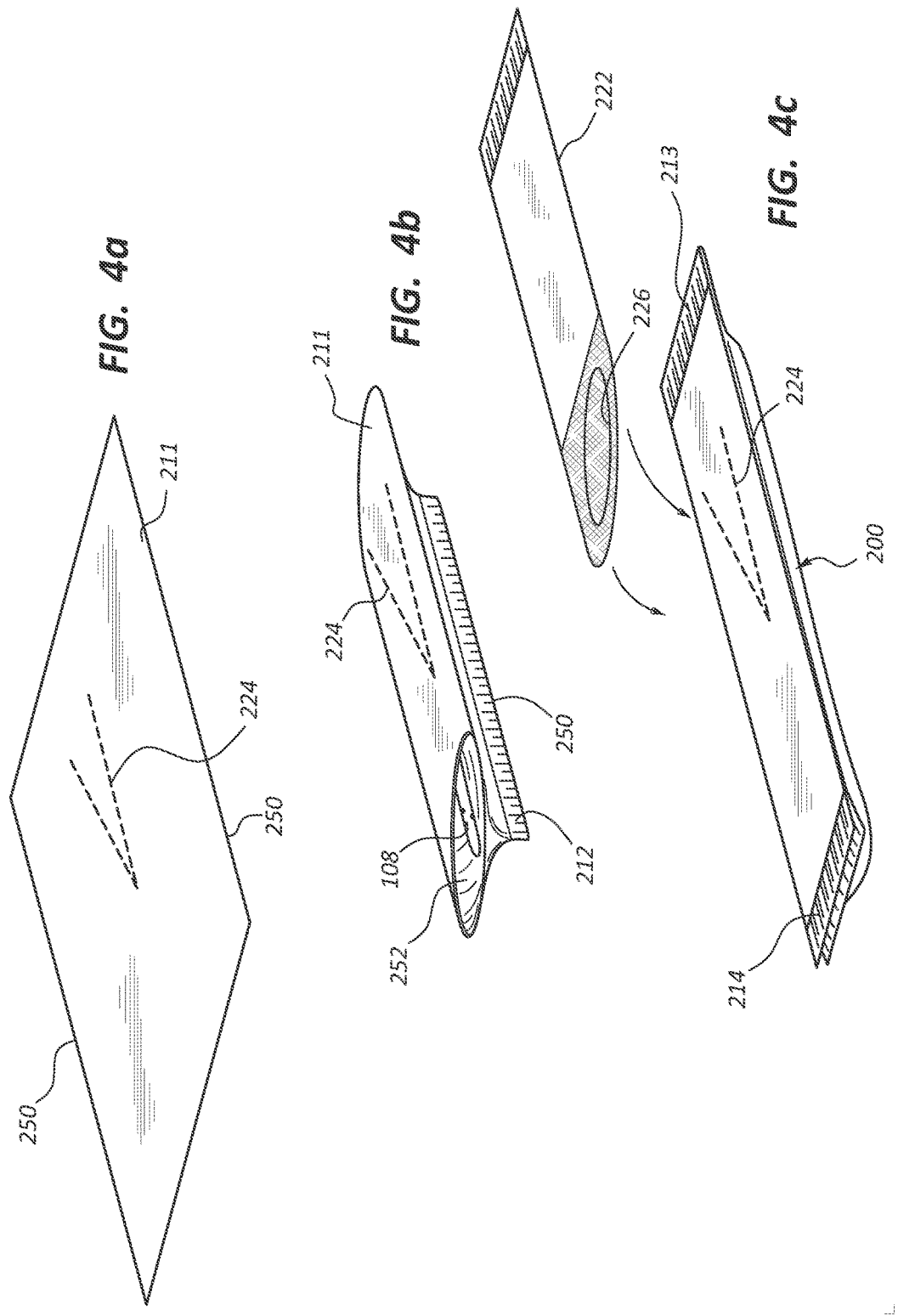

URINARY CATHETER

PRIORITY

This application is a continuation-in-part of U.S. patent application Ser. No. 15/506,723, filed Feb. 24, 2017, which is a U.S. National Stage Patent Application under 35 USC § 371 of International Patent Application No. PCT/US 2015/047026, filed Aug. 26, 2015, which claims the benefit of priority to U.S. Provisional Patent Application No. 62/042,125, filed Aug. 26, 2014, each of which is incorporated herein by reference in its entirety into this application.

BACKGROUND

People suffering from neurogenic bladder disorders like spinal cord injury, spina bifida or multiple sclerosis, and non-neurogenic bladder disorders like obstruction due to prostate enlargement, urethral strictures or post-operative urinary retention, need to be continuously catheterized to empty their urinary bladders. However, continuous catheterization can lead to problems like urinary tract infections (UTI), urethral strictures or male infertility. Intermittent catheterization at regular intervals avoids many of the negative effects of continuous long term catheterization. There are four primary categories for intermittent catheters: (1) Bare Intermittents, (2) Hydrophilic Coated Intermittents, (3) Pre-Wetted Intermittents, and (4) Catheter in Bag or "Touchless" Intermittents.

Bare Intermittents require the use of an external lubrication method. These catheters are the least expensive and most commonly used. Typical materials include natural rubber (latex) (NRL), polyvinyl chloride (PVC) and silicone. The common lubrication method is a gel pack. The gel is either applied to the meatus of the urethra or the tip of the catheter itself. Hydrophilic Coated Intermittents have a lubricious coating applied typically to the first two-thirds of the shaft of the catheter and are activated by breaking a water sachet located inside the package prior to opening the package. When activated, the catheter is lubricious for insertion into the urethra. Potential issues with the Bare Intermittents and the Hydrophilic Coated Intermittents include the amount of mess they create (e.g., from the excess water from the water sachet and lubricant from the lubricant packs) and the time required for the user to complete the voiding process.

Pre-Wetted Intermittents may be packaged in a non-permeable package (e.g. foil, or rigid plastic) and suspended in water. Ideally, the catheters will stay wet over the length of their shelf life and may be much like hydrophilic coated intermittents that have been activated by water. Pre-Wetted Intermittents may have a lubricious coating in addition to being packaged in water. This can eliminate the process step of lubricating the catheter, but may still cause some mess to contend with (e.g., from the water stored in the package), and the coating may dry out over its shelf life making it unusable.

Catheter in Bag or "Touchless" Intermittents may include either a Bare Intermittent or Hydrophilic Coated Intermittent. There may be an insertion tip on an end of the bag with the distal end of the catheter captured in the insertion tip. Upon use, the user may advance the catheter out of the bag using the insertion tip to help guide the catheter into the urethra. The bag may be used for urine collection. However, use of a Touchless Catheter may be cumbersome and difficult.

The following are references relating to coatings: U.S. Pat. No. 6,673,053, U.S. Pat. No. 8,011,505, and U.S. Pat. No. 6,059,107, which are incorporated by reference herein.

SUMMARY

The urinary catheters described herein provide a novel type of intermittent catheter not currently available. The coating may exhibit hygroscopic characteristics, described herein as the characteristic or intention of the coating to not only retain the moisture inherent in the coating but also to attract moisture from the environment. The coating may exhibit hydrophilic characteristics. The coating described herein is an improved formulation that is applied in a wet state and stays wet for an extended period of time. Accordingly, the urinary catheters described herein do not require an additional lubricant or wetting component, such as a water sachet or gel package, to accompany the catheters in the containers. The urinary catheters described herein may be packaged individually in a discrete container, such as an opaque foil. These and other features of embodiments of the present invention will become more fully apparent from the following description and appended claims, or may be learned by the practice of embodiments of the invention as set forth hereinafter.

In one embodiment a urinary catheter may include a catheter shaft attached to a handle. The urinary catheter may also include a hygroscopic and/or hydrophilic coating disposed on an outer surface of the catheter shaft. The coating may include a hydrogel, glycerin or water, and a polyethylene glycol (PEG). In one embodiment, the hydrogel may be LUBRAJEL® RR CG hydrogel or LUBRAJEL® RR hydrogel, and the PEG may be one or both of PEG 300 and PEG 400. In embodiments described herein with respect to specific hydrogels (e.g., LUBRAJEL® RR CG hydrogel), other hydrogels (e.g., LUBRAJEL® RR hydrogel) are contemplated as being substituted for, or added to, the specified hydrogel. Likewise, in embodiments described herein with respect to specific polyethylene glycols (e.g., PEG 300), other polyethylene glycols are contemplated as being substituted for, or added to, the specified polyethylene glycol.

In one embodiment, a urinary catheter includes a catheter shaft attached to a handle, and a first coating disposed on an outer surface of the catheter shaft, the first coating including a hydrogel or polyacrylic acid (PAA), glycerin and/or water, and polyethylene glycol (PEG), the first coating exhibiting hygroscopic and/or hydrophilic characteristics. In one embodiment, the outer surface of the catheter shaft includes a second coating over which the first coating is disposed. In one embodiment, the second coating is a hydrophilic coating.

In one embodiment, the coating formulations described herein provide non-adhesion (or anti-blocking) toward the packaging material. In one embodiment, a catheter with the coating can be sterilized through electron beam ("e-beam") sterilization or ethylene oxide (EtO) sterilization. In one embodiment, an additional ultraviolet (UV)-curable silicone film can be applied over a catheter with the coating described herein. The silicone film may restrict the coating on the catheter. In one embodiment, the film may be moved, e.g., toward the catheter handle, thereby acting as a touchless layer while maintaining the lubricity of the catheter. In one embodiment, the UV-curable silicone film is disposed on the coating via an UV curing process.

In one embodiment of the packaged urinary catheter, a coating formulation (e.g., a formulation for a base coating and/or outer coating) for the catheter may include LUB- RAJEL® RR CG hydrogel in a range of 15 wt % to 35 wt %, water in a range of 10 wt % to 45 wt %, and PEG in a range of 20 wt % to 75 wt %. In one embodiment, a coating formulation may include LUBRAJEL® RR CG hydrogel in a range of 20 wt % to 30 wt %, water in a range of 20 wt % to 30 wt %, and PEG 400 in a range of 40 wt % to 60 wt %. In one embodiment, the coating formulation may include LUBRAJEL® RR CG hydrogel in a range of 22 wt % to 26 wt %, water 25 wt %, and PEG 400 in a range of 49 wt % to 53 wt %. In one embodiment the coating formulation may include LUBRAJEL® RR CG hydrogel at 23.5 wt %, water at 25 wt %, and PEG 400 at 51.5 wt %. In one embodiment, a coating formulation may include LUBRAJEL® RR CG hydrogel in a range of 20 wt % to 30 wt %, glycerin in a range of 20 wt % to 30 wt %, and PEG 400 in a range of 40 wt % to 60 wt %. In one embodiment, the coating formulation may include LUBRAJEL® RR CG hydrogel in a range of 20 wt % to 30 wt %, glycerin in a range of 40 wt % to 60 wt %, and PEG 300 in a range of 20 wt % to 30 wt %. In one embodiment, the coating formulation may include LUBRAJEL® RR CG hydrogel in a range of 10 wt % to 35 wt %, glycerin in a range of 25 wt % to 75 wt %, PEG 300 in a range of 25 wt % to 65 wt %, and PEG 400 in a range of 25 wt % to 50 wt %. In one embodiment, a coating formulation may include LUBRAJEL® RR CG hydrogel in a range of 20 wt % to 30 wt %, glycerin in a range of 40 wt % to 60 wt %, propylene glycol (PEG) in a range of 10 wt % to 15 wt %, and ethanol (anhydrous) in a range of 10 wt % to 15 wt %. In one embodiment, the LUBRAJEL® RR CG hydrogel is 50 wt %, the glycerin is 25 wt %, and both the PEG and ethanol are 12.5 wt %.

In one embodiment, a coating formulation may include LUBRAJEL® RR hydrogel in a range of 15 wt % to 35 wt %, glycerin in a range of 15 wt % to 30 wt %, and PEG 400 in a range of 35 wt % to 70 wt %. In one embodiment, the coating formulation may include LUBRAJEL® RR hydrogel at 25 wt %, glycerin at 25 wt %, and both PEG 300 and PEG 400 at 25 wt %. In one embodiment, the coating formulation may include LUBRAJEL® RR hydrogel at 40 wt %, glycerin at 15 wt %, PEG 300 at 15 wt %, and PEG 400 at 30 wt %. In one embodiment, a coating formulation may include LUBRAJEL® RR in a range of 20 wt % to 30 wt %, water in a range of 20 wt % to 30 wt %, and PEG 400 in a range of 40 wt % to 60 wt %.

In one embodiment, a coating formulation may include polyacrylic acid (PAA) in a range of 0.2 wt % to 3 wt %, glycerin in a range of 15 wt % to 25 wt %, water in a range of 20 wt % to 30 wt %, and PEG 400 in a range of 40 wt % to 60 wt %. In one embodiment, a coating formulation may include PAA in a range of 0.1 wt % to 2.5 wt %, water in a range of 10 wt % to 45 wt % and PEG, such as PEG 300 and/or PEG 400, in a range of 20 wt % to 65 wt %.

In one embodiment, a silicone film may be formed over a coating on a catheter. In one embodiment, a method of forming a catheter with a coating includes dipping a coated catheter, such as a hydrophilic coated catheter, into a solution containing any of the coating formulations herein, such as a coating formulation including PAA, water, and PEG or a coating formulation including hydrogel, glycerin and/or water, and PEG, then dipping the twice-coated catheter into a UV curable solution, then exposing the coated areas to a UV source, and then directly placing the catheter into a package. In one embodiment, the hydrophilic coated catheter is dipped into a PAA/water/PEG solution for a dwell time in a range of 0.1 seconds to 10 seconds. In one embodiment, after the catheter is dipped into the PAA/water/PEG solution, it is dipped into a silicone solution with UV curable agents several times to achieve a desired film thickness. In one embodiment, the desired thickness is 0.001 in. to 0.004 in. In one embodiment, the catheter is dipped into the silicone solution with UV curable agents 2 to 6 times. In one embodiment, after being dipped into the silicone solution with UV curable agents, the catheter is exposed to a UV source, such as a UV light, in a time range of 0.3 min to 2.0 min. In one embodiment, following the exposure to the UV source, the catheter is placed directly into a film, foil, and/or Tyvek package without a further drying process.

In one embodiment, a method of making a urinary catheter includes applying a first coating to a catheter shaft, the first coating comprising a hydrogel or polyacrylic acid (PAA), glycerin and/or water, and polyethylene glycol (PEG) to form a coated catheter, and placing the coated catheter into a package comprising a gas impermeable foil material. In one embodiment, the catheter shaft includes a base hydrophilic coating, and the first coating is applied over the base hydrophilic coating. In one embodiment, the applying includes dipping the catheter shaft with the base hydrophilic coating into a solution containing a formulation of the first coating. In one embodiment, the first coating formulation comprises only the PAA, the water, and the PEG, further comprising dipping the coated catheter into a silicone solution including ultraviolet (UV) curable agents to form a silicone film over the first coating. In one embodiment, the method includes exposing the silicone film to a UV light source for a period of time to cure the silicone solution.

In one embodiment, the urinary catheter may include an eyelet or a plurality of staggered, opposing eyelets (e.g., 3, 4, 5, 6, 7, 8, or more eyelets) proximal to a catheter tip, the eyelets may be arranged in a variety of ways, including circumferentially positioned about 90 degrees apart and positioned in a non-overlapping configuration. In one embodiment, the urinary catheter shaft includes a funnel shaped proximal end and ridges configured to facilitate gripping. In one embodiment, the urinary catheter may have a coating that exhibits hygroscopic characteristics. In another embodiment, the urinary catheter may have a coating that exhibits hydrophilic characteristics.

In one embodiment, a packaged urinary catheter may include a container and a urinary catheter. The urinary catheter may include a catheter shaft attached to a handle and a coating disposed on an outer surface of the catheter shaft. In one embodiment, the coating may include a hydrogel, glycerin or water, and PEG, such as one or both of PEG 300 and PEG 400. In one embodiment, the coating may include PAA, glycerin, water, and PEG, such as PEG 300 and/or PEG 400. In one embodiment, the coating may include PAA, water, and PEG, such as PEG 300 and/or PEG 400.

In one embodiment of the packaged urinary catheter, the container may include a gas impermeable foil material. In one embodiment of the packaged urinary catheter, the container may include an adhesive tab covering a perforated section of the foil material, the adhesive tab may include a pull loop. In one embodiment, the container may include a water sachet, gel package, or other type of lubricant therein. In one embodiment, the container may include a moisture source (in contact or separated from the catheter) from which a hygroscopic coating and/or a hydrophilic coating on the urinary catheter may absorb or obtain moisture. In one embodiment of the packaged urinary catheter, the container does not include any water sachet, gel package, or other type of lubricant or moisture source therein.

In one embodiment, a method of catheterizing may include obtaining a urinary catheter that may include a handle and a catheter shaft. The catheter shaft may include a hydrophilic coating and/or a hygroscopic coating on an outer surface thereof. In one embodiment, the coating may include a coating formulation described herein. The method may further include inserting the urinary catheter into a bladder. In one embodiment, the method of catheterizing may include obtaining the urinary catheter from a container in which the urinary catheter has been stored. In one embodiment, the method of catheterizing does not include application of a lubricant or water to the catheter shaft at any time prior to insertion into the bladder, including while in the package.

Also provided herein is a urinary catheter including, in some embodiments, a handle and a catheter shaft attached to the handle. The handle includes a plurality of ridges configured to facilitate gripping the handle. The handle also includes one or more loops integral with the handle configured for manipulating the catheter during at least catheterization. The catheter shaft includes opposing eyelets proximate a tip of the catheter shaft in fluid communication with an opening in a proximal end of the handle by a lumen disposed in the catheter connecting the catheter shaft and the handle.

In such embodiments, a first plane including a transverse cross-section of the handle is orthogonal to a second plane including at least one opening of the one or more loops.

In such embodiments, the handle is configured to rest in a hand of a patient or a caregiver while the one or more loops respectively receive one or more fingers of the patient or the caregiver.

In such embodiments, the one or more loops are respectively one or more rings, each attached to the handle by a tab extension of the handle.

In such embodiments, the opposing eyelets include at least two pairs of staggered eyelets, the at least two pairs of eyelets staggered along a length of the catheter shaft and offset by about 90 degrees around the catheter shaft in a non-overlapping configuration.

In such embodiments, the catheter further includes a hydrophilic base coating over the catheter shaft, the base coating of PAA in a range of 0.2 wt % to 3 wt %, glycerin in a range of 15 wt % to 25 wt %, water in a range of 20 wt % to 30 wt %, and PEG 400 in a range of 40 wt % to 60 wt %.

In such embodiments, the catheter further includes a hydrophilic base coating over the catheter shaft, the base coating of PAA in a range of 0.1 wt % to 2.5 wt %, water in a range of 10 wt % to 45 wt %, and PEG in a range of 20 wt % to 65 wt %.

In such embodiments, the catheter further includes a hygroscopic outer coating over the catheter shaft, the outer coating of a hydrogel in a range of 20 wt % to 30 wt %, glycerin in a range of 20 wt % to 30 wt %, and PEG 400 in a range of 40 wt % to 60 wt %.

In such embodiments, the catheter further includes a hygroscopic outer coating over the catheter shaft, the outer coating of a hydrogel in a range of 20 wt % to 30 wt %, glycerin in a range of 40 wt % to 60 wt %, and PEG 300 in a range of 20 wt % to 30 wt %.

In such embodiments, the catheter further includes a hygroscopic outer coating over the catheter shaft, the outer coating of a hydrogel in a range of 10 wt % to 35 wt %, glycerin in a range of 25 wt % to 75 wt %, PEG 300 in a range of 25 wt % to 65 wt %, and PEG 400 in a range of 25 wt % to 50 wt %.

In such embodiments, the catheter further includes a hygroscopic outer coating over the catheter shaft, the outer coating of a hydrogel in a range of 15 wt % to 35 wt %, water in a range of 10 wt % to 45 wt %, and PEG 400 in a range of 20 wt % to 75 wt %.

In such embodiments, the catheter further includes a hygroscopic outer coating over the catheter shaft, the outer coating of a hydrogel in a range of 22 wt % to 26 wt %, water in a range of 25 wt %, and PEG 400 is in a range of 49 wt % to 53 wt %.

Also provided herein is a urinary catheter including, in some embodiments, a handle and a catheter shaft attached to the handle. The handle includes a plurality of ridges configured to facilitate gripping the handle. The handle also includes one or more loops integral with the handle configured for manipulating the catheter during at least catheterization. A first plane including a transverse cross-section of the handle is orthogonal to a second plane including at least one opening of the one or more loops. The catheter shaft includes opposing eyelets proximate a tip of the catheter shaft in fluid communication with an opening in a proximal end of the handle by a lumen disposed in the catheter connecting the catheter shaft and the handle.

In such embodiments, the one or more loops are respectively one or more rings, each attached to the handle by a tab extension of the handle.

In such embodiments, the opposing eyelets include at least two pairs of staggered eyelets, the at least two pairs of eyelets staggered along a length of the catheter shaft and offset by about 90 degrees around the catheter shaft in a non-overlapping configuration.

Also provided herein is a urinary catheter package including, in some embodiments, a urinary catheter and packaging for the catheter. The catheter includes a catheter shaft attached to a catheter handle. The handle includes one or more loops integral with the handle configured for manipulating the catheter during at least catheterization. A first plane including a transverse cross-section of the handle is orthogonal to a second plane including at least one opening of the one or more loops. The catheter shaft includes opposing eyelets proximate a tip of the catheter shaft in fluid communication with an opening in a proximal end of the handle by a lumen disposed in the catheter connecting the catheter shaft and the handle. The packaging includes an adhesive pull tab over a perforated area of the packaging configured to expose the catheter disposed in the packaging when the pull tab is pulled.

In such embodiments, the one or more loops of the catheter handle are respectively one or more rings, each attached to the handle by a tab extension of the handle.

In such embodiments, the opposing eyelets in the tip of the catheter shaft include at least two pairs of staggered eyelets, the at least two pair of eyelets staggered along a length of the catheter shaft and offset by about 90 degrees around the catheter shaft in a non-overlapping configuration.

In such embodiments, the urinary catheter further includes a hydrophilic base coating including PAA over the catheter shaft, a hygroscopic outer coating including a hydrogel over the catheter shaft, or a combination of the hygroscopic outer coating over the hydrophilic base coating over the catheter shaft.

In such embodiments, the urinary catheter further includes a UV-cured silicone film over at least a portion of the hydrophilic base coating, the hygroscopic outer coating, or the combination of the hygroscopic outer coating and the hydrophilic base coating.

BRIEF DESCRIPTION OF THE DRAWINGS

The disclosed systems and methods can be better understood with reference to the following drawings. The components in the drawings are not necessarily to scale. It is appreciated that these drawings depict only typical embodiments of the invention and are therefore not to be considered limiting of its scope. Example embodiments of the invention will be described and explained with additional specificity and detail through the use of the accompanying drawings in which:

FIG. 1 shows one embodiment of a urinary catheter according to embodiments described herein, and illustrates the exemplary use of a male urinary catheter according to embodiments described herein.

FIG. 2 shows one embodiment of a urinary catheter according to embodiments described herein, and illustrates the exemplary use of a female urinary catheter according to embodiments described herein.

FIG. 3a is a urinary catheter according to embodiments described herein.

FIG. 3b is a cross sectional view of the urinary catheter shaft according to embodiments described herein.

FIG. 4a is a first step in a method of making the container for a urinary catheter according to embodiments described herein.

FIG. 4b is a second step in a method of making the container for a urinary catheter according to embodiments described herein.

FIG. 4c is a third step in a method of making the container for a urinary catheter according to embodiments described herein.

Figure 5:
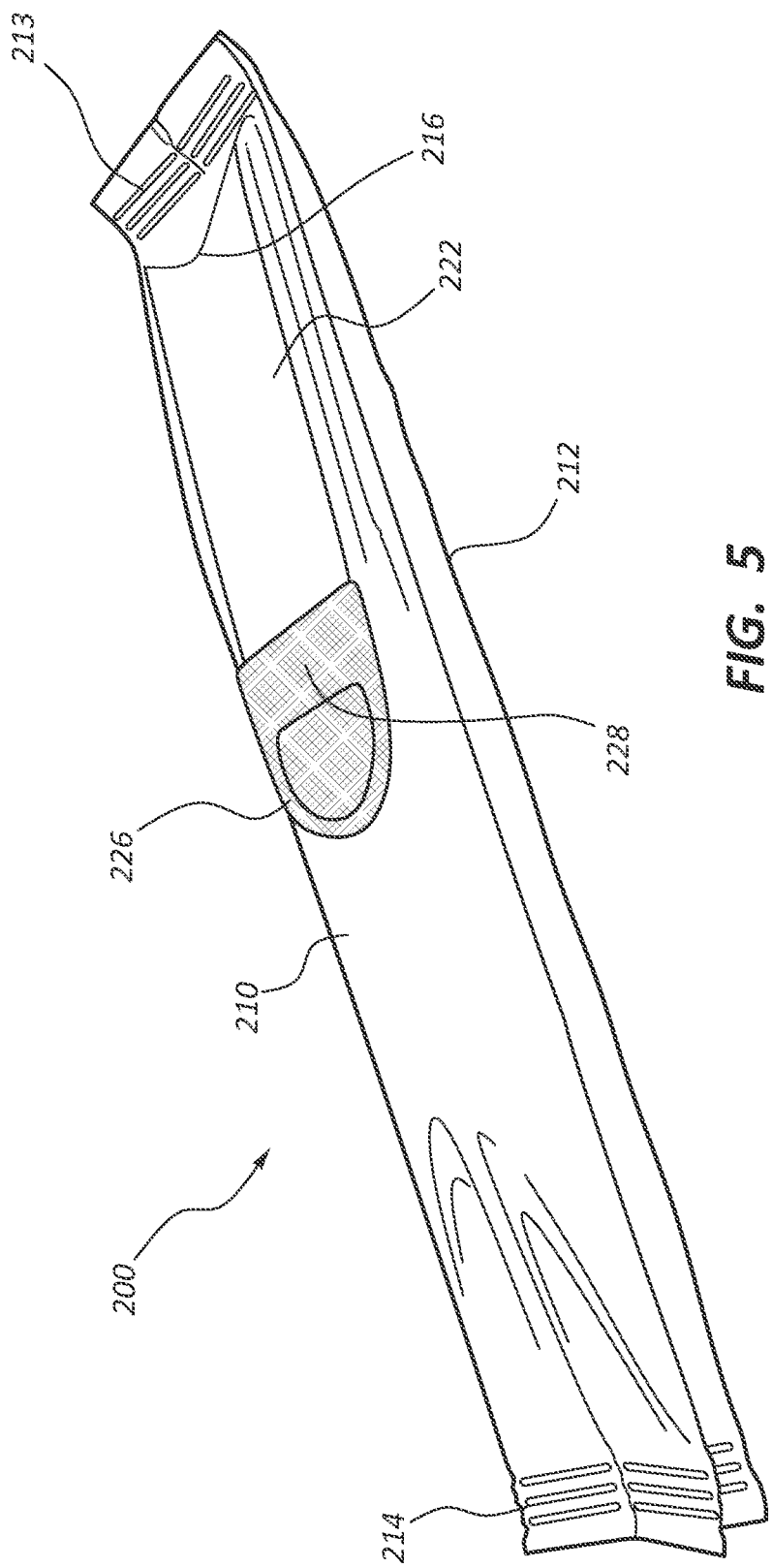
FIG. 5 is a container for a urinary catheter of FIGS. 4-7, according to embodiments described herein in a closed state.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but rather the intention is to cover all modifications, equivalents, and alternatives falling within the spirit and scope of the invention as defined by the appended claims.

DETAILED DESCRIPTION

The following description and accompanying figures, which describe and show certain embodiments, are made to demonstrate, in a non-limiting manner, several possible configurations of a catheter according to various aspects and features of the present disclosure. While the description herein, by way of example, is focused primarily on a description of a urinary catheter and associated methods, the inventions described herein are not so limited and the concepts may be applied to other types of catheters and devices.

The urinary catheter described herein is ready to use immediately when the container is opened, and may be inserted by the patient or patient's caregiver in a homecare setting, managed care/assisted living setting, or in hospitals. Within the homecare setting, the catheter can be used in a range of restroom and non-restroom environments. FIGS. 1 and 2 show urinary catheters and methods of using them according to embodiments described herein.

FIG. 1 illustrates the male urinary catheter 10, the packaging 20 for the male urinary catheter 10, and the exemplary use (e.g., steps 30-33) thereof according to embodiments described herein, and FIG. 2 illustrates the female urinary catheter 50, the packaging 60 for the female urinary catheter 50, and the exemplary use (e.g., steps 70-73) thereof according to embodiments described herein. The methods shown in FIGS. 1 and 2 do not require the user to take any step to apply lubricant, such as water or gel, directly to the catheter, either while the catheter is within the package or when after the package has been opened. Accordingly, the user may move directly from the step of removing the catheter from the package 30, 70 to the step of inserting the catheter 32, 72 without an intervening direct lubrication or hydration step (see example steps 31, 71, which indicate the catheter is ready to use upon removing from the packaging, without requiring the addition of water or lubricant). The catheters used in FIGS. 1 and 2 can be catheters of any of the embodiments discussed herein, e.g., the catheters may have a coating formulation that exhibits hygroscopic and/or hydrophilic characteristics (which eliminates the need for the user to take steps to lubricate or hydrate the catheter). In the case of a catheter with a hygroscopic coating, while some water from the surrounding environment may be naturally attracted by the coating, this is not considered a direct lubrication or hydration step taken in the method. After use, the catheter 10, 50 may be disposed of according to sanitary procedure. Example disposal steps 33, 73 depict one possible procedure for disposal, including returning the catheter to the packaging and discarding the packaging in a trash can or similar receptacle. The packaging may be sealable (e.g., by adhesive, zip-lock, etc.), such that the package may be sealed shut after the urinary catheter is disposed therein.

Referring to FIG. 3a, in one embodiment, a urinary catheter 100 includes a handle 102 on a proximal end and a catheter shaft 104 attached to the handle 102. The urinary catheter may be one of a variety of different types of urinary catheters. The handle 102 may have a funnel-like shape 106 on the proximal end thereof, and may be adapted to connect to drain bags, extension tubes, and/or the like. Also, handle shapes other than a funnel-like shape may be utilized within the scope of the present disclosure. The handle 102 may indicate the size of the catheter, and may have a color to indicate sex (e.g., pink for female, blue for male). In one embodiment, the catheter shaft 104 is made from a silicone material. In one embodiment, the silicone material has a durometer in the range of shore 70 A to 85 A and a thickness in the range of 1.1 mm to 2.27 mm. It is appreciated that the composition of the catheter shaft 104 may include other materials that possess similar physical properties which falls within scope of the present disclosure. In one embodiment, the column strength of the catheter shaft 104 is configured or designed to facilitate insertion, e.g., requiring less force than current polyvinyl chloride (PVC) catheters. In one embodiment, the catheter 100 will be at least partially transparent to an unaided eye.

Referring to FIGS. 3a and 3b, the catheter 100 includes openings 114 in a distal end 110 that are in fluid communication with a lumen 150 that extends through the catheter shaft and handle. In one embodiment, the catheter includes four staggered, opposing eyelets 114 proximate a catheter tip 108, the eyelets 114 are circumferentially positioned about 90 degrees apart and positioned in a non-overlapping configuration. It is appreciated that other numbers and configurations of openings fall within the scope of the present disclosure. The handle 102 includes ridges 112 to provide a gripping surface for easier gripping and handling. The catheter shaft 104 may include the lumen 150, a catheter wall 152, a hydrophilic base coating 154 (e.g., polyacrylic acid), and may also include a pre-hydrated outer coating applied thereover 156 (e.g., over the base coating). The pre-hydrated coating may remain wet without the application of water or lubricant gel.

In one embodiment, the catheter 100 includes a hygroscopic coating 156 (e.g. a top or outer pre-hydrated coating). In one embodiment, the catheter 100 includes a hygroscopic coating 156 including a hydrogel, glycerin, water, and a polyethylene glycol (PEG) with a molecular weight equal to or less than 600, for example one or more of polyethylene glycol (PEG) 300 and PEG 400. In one embodiment, the hydrogel is a LUBRAJEL® hydrogel. For coating embodiments described herein, the type of LUBRAJEL® hydrogel may be LUBRAJEL® RR CG hydrogel, having an INCI name of Glycerin (and) Glyceryl Acrylate/Acrylic Acid Copolymer (and) Propylene Glycol. For coating embodiments described herein, the type of LUBRAJEL® hydrogel may be LUBRAJEL® RR hydrogel. In one embodiment, the catheter includes a coating including a hydrogel (e.g., LUBRAJEL® hydrogel), glycerin, propylene glycol (PEG), and ethanol. In one embodiment, the catheter includes a coating including a hydrogel (e.g., LUBRAJEL® hydrogel), glycerin or water, and propylene glycol (PEG), such as PEG 300 and/or PEG 400. In one embodiment, the catheter may be sold and packaged in sizes ranging in diameter from 8 Fr to 24 Fr (e.g., 8 Fr, 10 Fr, 12 Fr, 14 Fr, 16 Fr, 18 Fr, 20 Fr, 22 Fr, 24 Fr) with a length L of greater than 155 mm and intended for female use. However, other sizes of catheters may also be used. In other embodiments, the catheter may be sold and packaged in various sizes for male use.

In one embodiment, the base coating 154 and/or the outer coating 156 may be applied to the catheter shaft by a method involving either dipping, brushing, spraying or extruding. It is appreciated that other methods of applying one or both of the coatings to the catheter may be utilized and fall within the scope of the present disclosure. In one embodiment, the catheter shaft may be dipped into a volume of coating formulation. In one embodiment, the components of the coating formulation are mixed together, then the catheter shaft dipped into the volume thereof. For example, the hydrophilic coating or outer coating may be produced by mixing LUBRAJEL® with water and PEG for between 1.5 to 4.0 hours. The catheter (with or without a base coating) may be dipped into the coating solution and left to dwell for between 0.1-10 seconds. The catheter may then be removed from the coating solution and directly placed into packaging without any further drying process.

In one embodiment, the eyelets are punched into the catheter prior to dipping into one or more coating formulations to form a coating (e.g., a base coating and/or outer coating) such that both interior and exterior of the catheter is coated, i.e., at least a portion of the outer surface of the catheter shaft and at least a portion of the inner wall defining the lumen 150 of the catheter shaft are coated with the coating formulation. In other embodiments, one or more coating formulations may be brushed onto an outer surface of the catheter shaft (e.g., doctor blade method). In one embodiment, the coating (e.g., the base coating and/or the outer coating) is only on the catheter shaft (either the entire catheter shaft or a distal portion thereof), not on the handle. The coating described herein provides the urinary catheter with a coefficient of friction (COF) in the range of 0.03 to 0.15.

In one embodiment, a coating formulation (e.g., a formulation for a base coating and/or outer coating) for the catheter may include LUBRAJEL® RR CG hydrogel in a range of 15 wt % to 35 wt %, water in a range of 10 wt % to 45 wt %, and PEG in a range of 20 wt % to 75 wt %. In one embodiment, a coating formulation may include LUBRAJEL® RR CG hydrogel in a range of 15 wt % to 35 wt %, water in a range of 2 wt % to 45 wt %, and PEG in a range of 20 wt % to 75 wt %. In one embodiment, a coating formulation may include LUBRAJEL® RR CG hydrogel in a range of 20 wt % to 30 wt %, water in a range of 20 wt % to 30 wt %, and PEG 400 in a range of 40 wt % to 60 wt %. In one embodiment, the coating formulation may include LUBRAJEL® RR CG hydrogel in a range of 22 wt % to 26 wt %, water 25 wt %, and PEG 400 in a range of 49 wt % to 53 wt %. In one embodiment the coating formulation may include LUBRAJEL® RR CG hydrogel at 23.5 wt %, water at 25 wt %, and PEG 400 at 51.5 wt %. In one embodiment, a coating formulation may include LUBRAJEL® RR CG hydrogel in a range of 20 wt % to 30 wt %, glycerin in a range of 20 wt % to 30 wt %, and PEG 400 in a range of 40 wt % to 60 wt %. In one embodiment, the coating formulation may include LUBRAJEL® RR CG hydrogel in a range of 20 wt % to 30 wt %, glycerin in a range of 40 wt % to 60 wt %, and PEG 300 in a range of 20 wt % to 30 wt %. In one embodiment, the coating formulation may include LUBRAJEL® RR CG hydrogel in a range of 10 wt % to 35 wt %, glycerin in a range of 25 wt % to 75 wt %, PEG 300 in a range of 25 wt % to 65 wt %, and PEG 400 in a range of 25 wt % to 50 wt %. In one embodiment, a coating formulation may include LUBRAJEL® RR CG hydrogel in a range of 20 wt % to 30 wt %, glycerin in a range of 40 wt % to 60 wt %, propylene glycol (PEG) in a range of 10 wt % to 15 wt %, and ethanol (anhydrous) in a range of 10 wt % to 15 wt %. In one embodiment, the LUBRAJEL® RR CG hydrogel is 50 wt %, the glycerin is 25 wt %, and both the PEG and ethanol are 12.5 wt %.

In one embodiment, a coating formulation may include LUBRAJEL® RR hydrogel in a range of 15 wt % to 35 wt %, glycerin in a range of 15 wt % to 30 wt %, and PEG 400 in a range of 35 wt % to 70 wt %. In one embodiment, the coating formulation may include LUBRAJEL® RR hydrogel at 25 wt %, glycerin at 25 wt %, and both PEG 300 and PEG 400 at 25 wt %. In one embodiment, the coating formulation may include LUBRAJEL® RR hydrogel at 40 wt %, glycerin at 15 wt %, PEG 300 at 15 wt %, and PEG 400 at 30 wt %. In one embodiment, a coating formulation may include LUBRAJEL® RR in a range of 20 wt % to 30 wt %, water in a range of 20 wt % to 30 wt %, and PEG 400 in a range of 40 wt % to 60 wt %.

In one embodiment, a coating formulation may include polyacrylic acid (PAA) in a range of 0.2 wt % to 3 wt %, glycerin in a range of 15 wt % to 25 wt %, water in a range of 20 wt % to 30 wt %, and PEG 400 in a range of 40 wt % to 60 wt %. In one embodiment, a coating formulation may include PAA in a range of 0.1 wt % to 2.5 wt %, water in a range of 10 wt % to 45 wt % and PEG, such as PEG 300 and/or PEG 400, in a range of 20 wt % to 65 wt %.

In one embodiment, a silicone film may be formed over a coating on a catheter. In one embodiment, a method of forming a catheter with a coating includes dipping a coated catheter, such as a hydrophilic coated catheter, into a solution containing any of the coating formulations herein, such as a coating formulation including PAA, water, and PEG or a coating formulation including hydrogel, glycerin and/or water, and PEG, then dipping the twice-coated catheter into a UV curable solution, then exposing the coated areas to a UV source, and then directly placing the catheter into a package. In one embodiment, the hydrophilic coated catheter is dipped into a PAA/water/PEG solution for a dwell time in a range of 0.1 seconds to 10 seconds. In one embodiment, after the catheter is dipped into the PAA/water/PEG solution, it is dipped into a silicone solution with UV curable agents several times to achieve a desired film thickness. In one embodiment, the desired thickness is 0.001 in. to 0.004 in. In one embodiment, the catheter is dipped into the silicone solution with UV curable agents 2 to 6 times. In one embodiment, after being dipped into the silicone solution with UV curable agents, the catheter is exposed to a UV source, such as a UV light, in a time range of 0.3 min to 2.0 min. In one embodiment, following the exposure to the UV source, the catheter is placed directly into a film, foil, and/or Tyvek package without a further drying process. The silicone with UV curable agents, after curing forms a film that covers the coating on the catheter and can be moved when the catheter is ready for insertion. This acts to facilitate insertion without touching the lubricious coating while maintaining the lubricity of the coating on the catheter.

Figure 6:
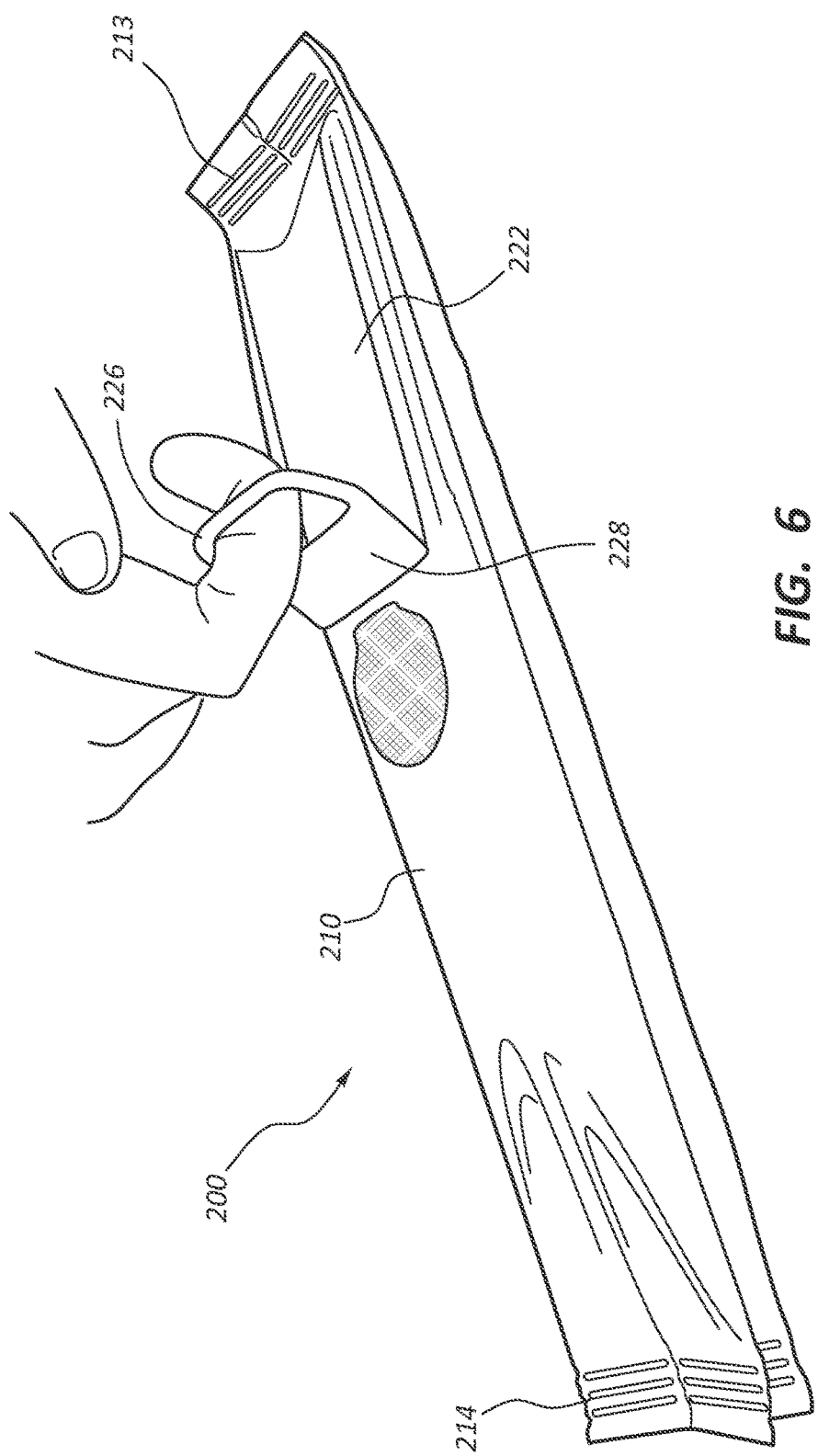
FIG. 6 is the container for a urinary catheter of FIGS. 4-7, being opened according to embodiments described herein.
Figure 7:
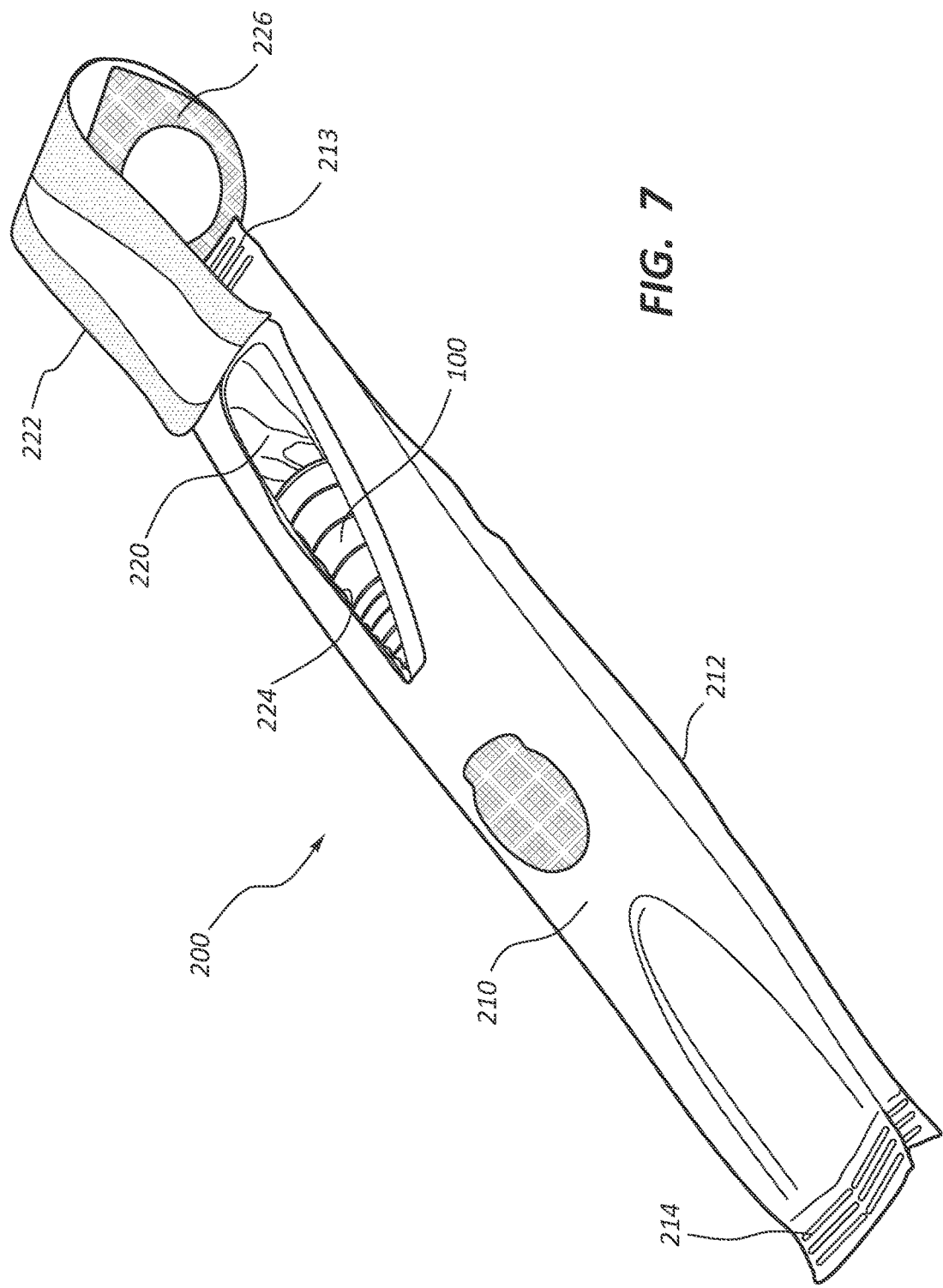
FIG. 7 is the container of FIGS. 4-7 in an opened state, revealing the urinary catheter handle.

Referring to FIGS. 4a-7, the urinary catheters described herein may be packaged individually in discrete containers to form packaged urinary catheters such as the packaged urinary catheter 200. For example, the packaging or container may be opaque and resemble an item distinct from a urinary catheter, such as a food item or the like. In one embodiment, the packaging or container 210 is formed of and/or includes a foil material. In other embodiments, the container 210 includes a polyolefin film (e.g., polyethylene (PE)), an ethylene vinyl acetate (EVA) film, and/or a metallized polypropylene (PP) film. In one embodiment, the packaging material is gas impermeable. In one embodiment, of the lubricity of the coating is maintained or improved over time in the packaging while at normal environmental storage conditions. The packaging 210 may have a color to indicate sex (e.g., pink for female, blue for male). In one embodiment, the packaging 210 can be sterilized either by Electron Beam Processing (E-beam) or treatment with Ethylene Oxide (EtO).

Referring to FIGS. 4a-4c, a method of manufacturing the packaging for a catheter, discussed herein, including the following steps of producing the package, performed in any order: providing a sheet material 211; providing a weakened area 224, such as a perforation or kiss cut, in the sheet material by cutting the material; folding over and connecting the longitudinal edges 250 of the sheet 211 to form a back seam 212 and a cavity 252 (FIG. 4b). Disposing a catheter 100 within the cavity 252 and enclosed therein by sealing the ends to create a first end seam 213, and a second end seam 214 (FIG. 4c). Adhering an adhesive tab 222 over the weakened area 224.

In one embodiment, this arrangement may be similar to a packaging such as might be used on a candy bar, with overlapping edges forming a seam along the back and seams at the edges. The overlapping edges may be folded to one side or the other. The packaging material may present a smooth front. The front of the container may include a sealed opening 220, covered by an adhesive tab 222 (FIG. 4c). The sealed opening may include a weakened area 224, such as a perforation or kiss cut, in the packaging material covered by an adhesive portion of the adhesive tab 222. The adhesive tab 222 may include features, such as a pull loop 226, to hang the container after exposing the catheter 100 in the packaging in order to facilitate user access to the catheter 100 in the container 210. The adhesive tab 222 may be formed of a material such as polyethylene terephthalate (PET) substrate, with an adhesive, such as an S6 adhesive, on part of or the entire bottom surface of the adhesive tab. In one embodiment, the adhesive tab may include a label. The label may have artwork printed on or otherwise associated with a top surface of the label. The label may be stamped out of a rollstock of material and a varnish may be applied over approximately 1 inch of the distal end 228 of the label to facilitate lifting to begin the peeling process.

The adhesive tab may include a pull loop 226 to facilitate opening of the container 210, which after opening (FIG. 7) may be positioned over a hook or the like in order to suspend the container for ease of use. Alternatively, the adhesive portion of the adhesive tab 222 may be pressed against a hard surface (e.g., a wall, table, desk, equipment, etc.) in order to prevent movement of the container. In one embodiment, the catheter 100 may be reinserted into the container 210 and the adhesive tab 222 pressed back over the opening 220 to re-seal the container 210 for disposal in another location. The embodiment of FIGS. 4-7 is easy to open by simply putting a finger through the pull loop 226 (FIG. 6) and pulling the adhesive tab toward the proximal end of container 216. The pulling action opens the container along the weakened area 224 to reveal the handle 102 of the catheter 100, which has a gripping surface to facilitate handling. Also, the container can be folded in half to minimize space needed to transport in a purse, bag, or the like.

Figure 8A:
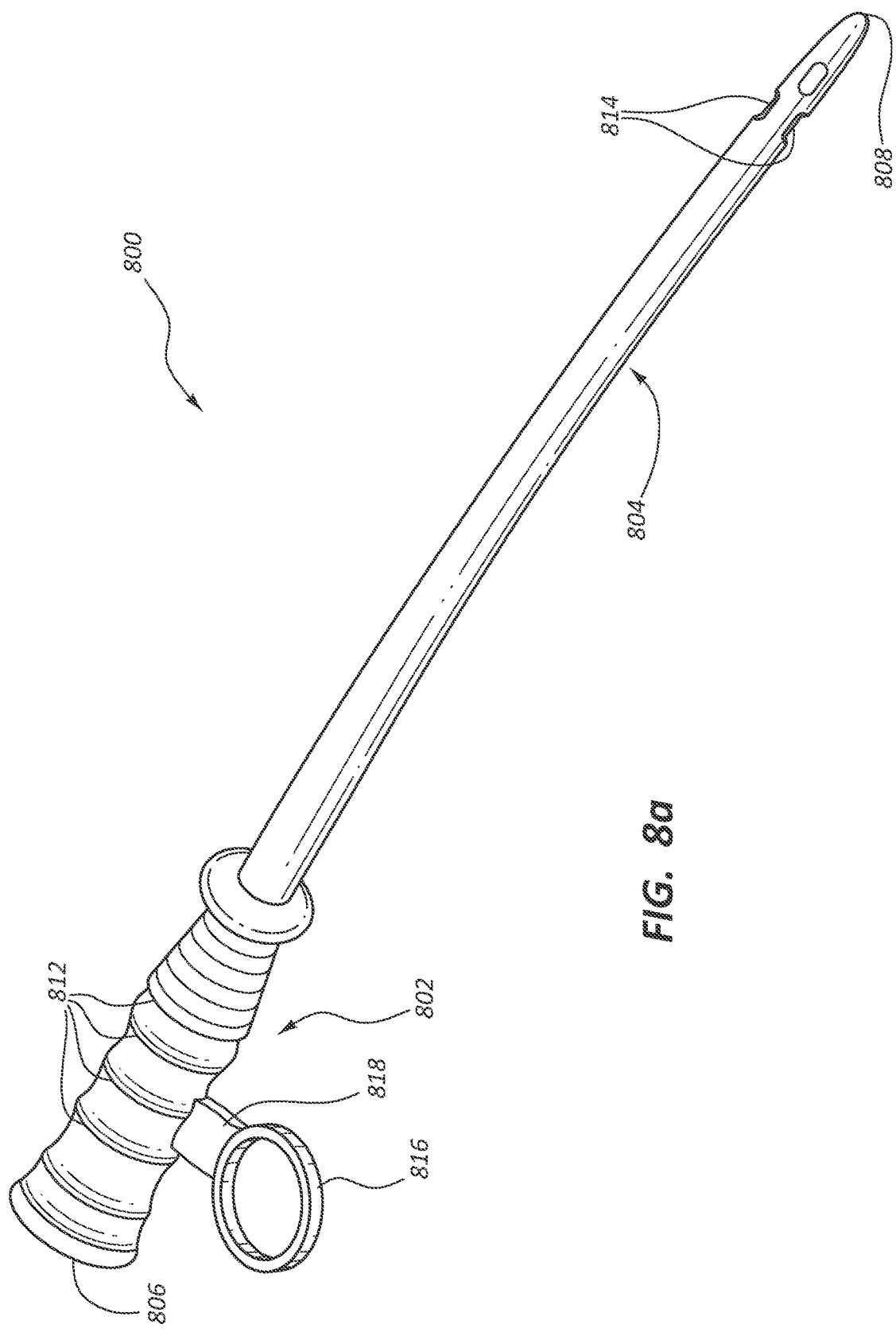
FIG. 8a provides a schematic illustrating a urinary catheter including a first loop for manipulating the catheter in accordance with some embodiments.
Figure 8B:
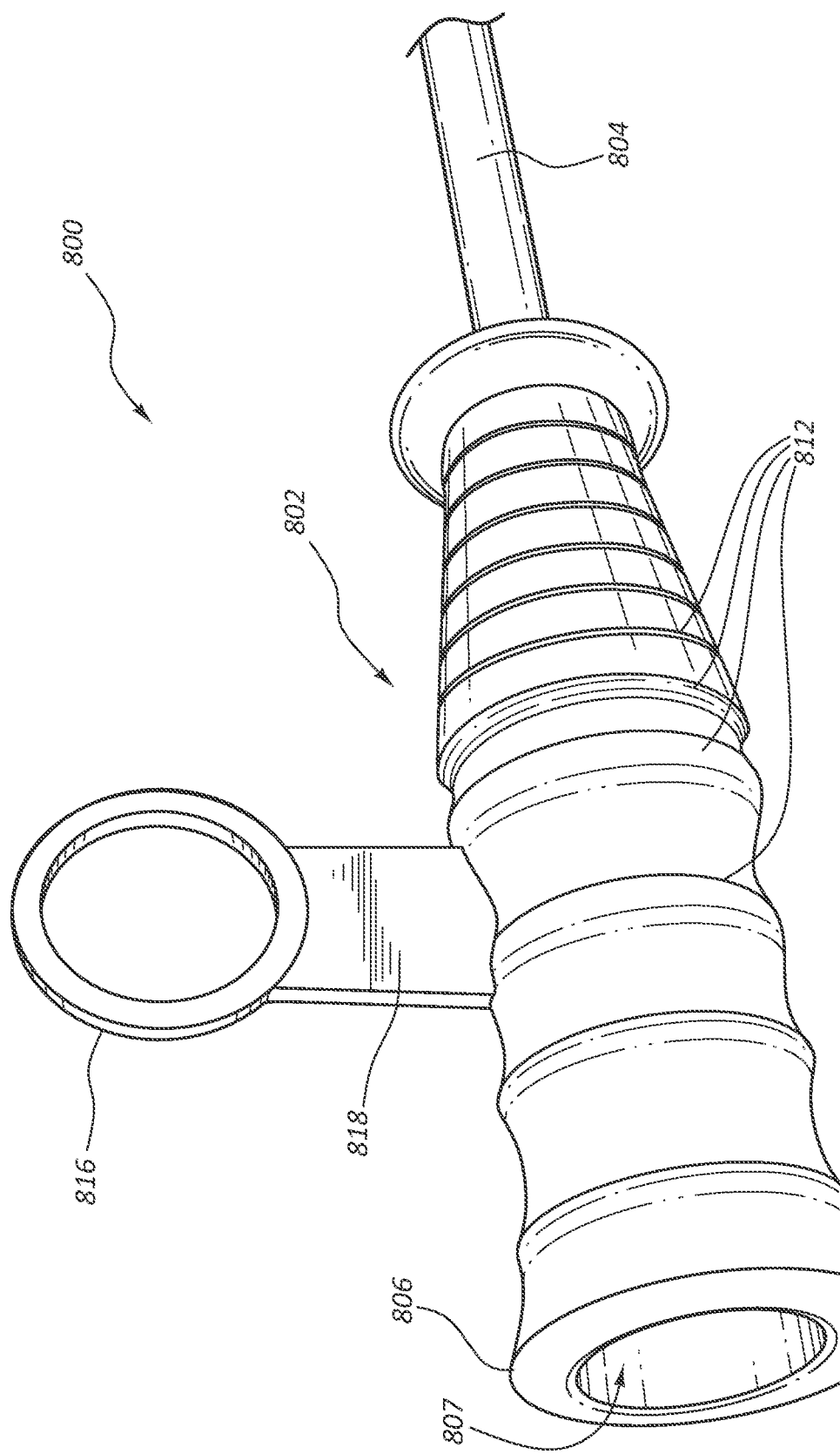
FIG. 8b provides a schematic illustrating a close-up view of a handle of the catheter of FIG. 8a in accordance with some embodiments.
Figure 8C:
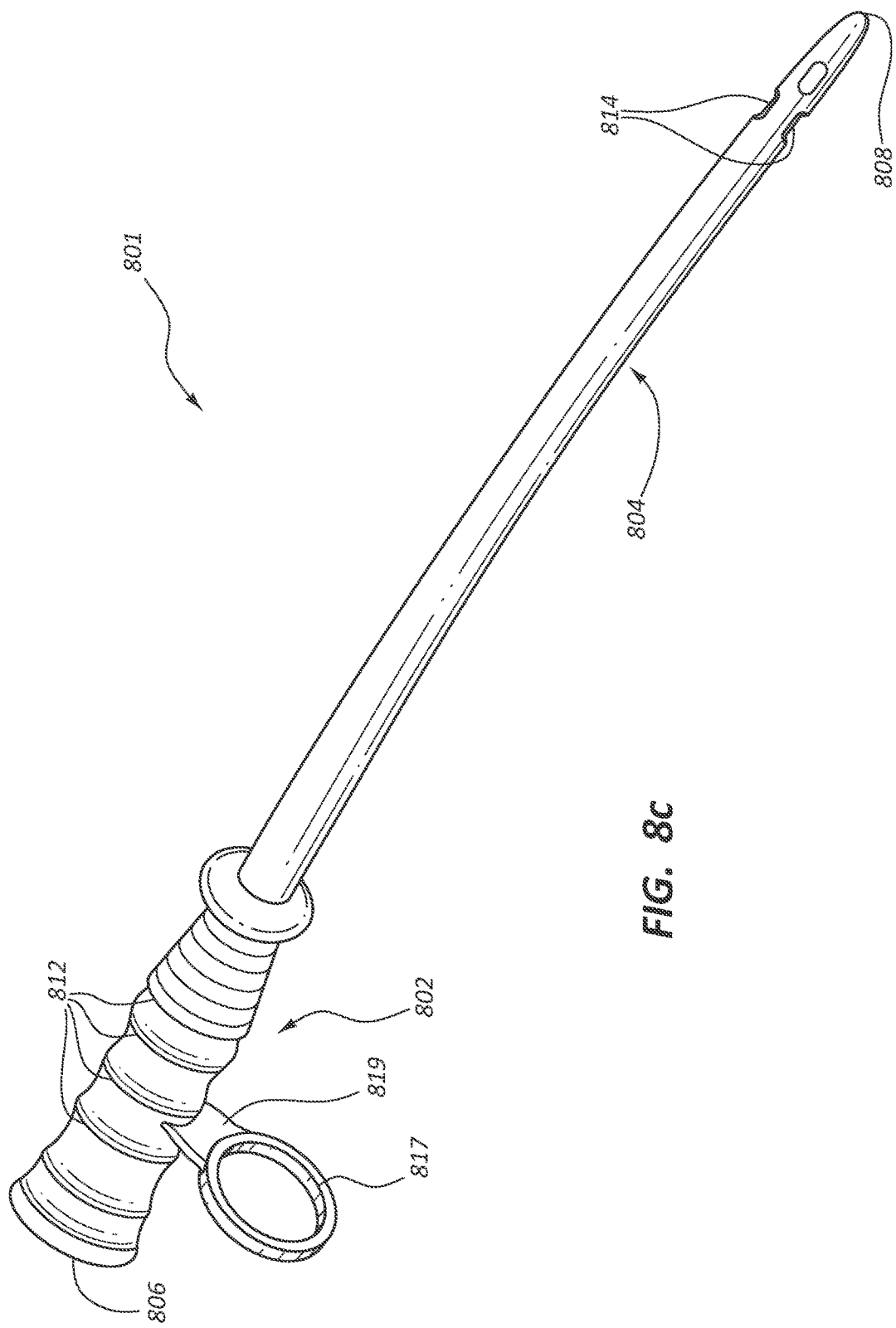
FIG. 8c provides a schematic illustrating a urinary catheter including a second loop for manipulating the catheter in accordance with some embodiments.
Figure 8D:
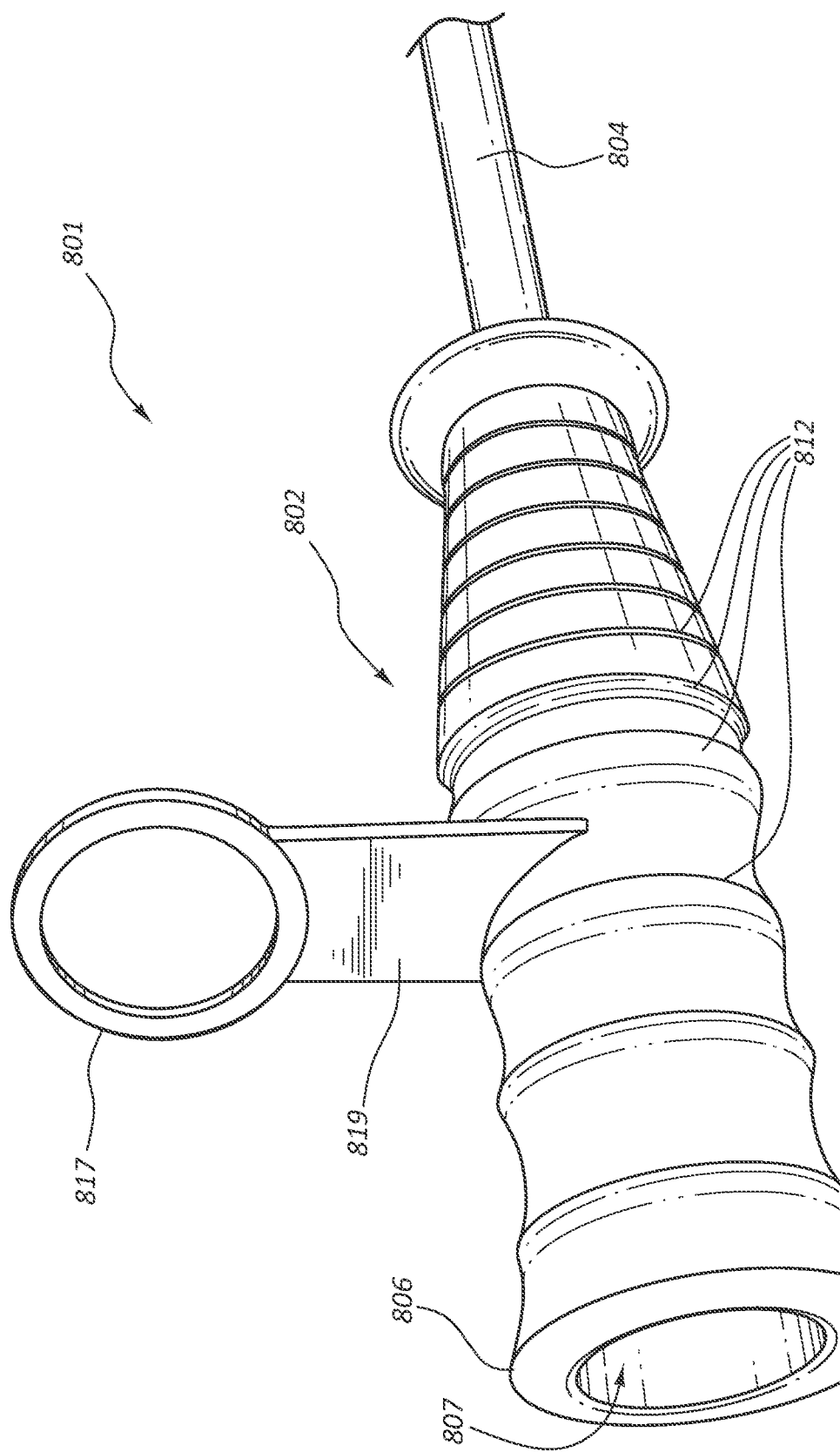
FIG. 8d provides a schematic illustrating a close-up view of a handle of the catheter of FIG. 8c in accordance with some embodiments.
Figure 9A:
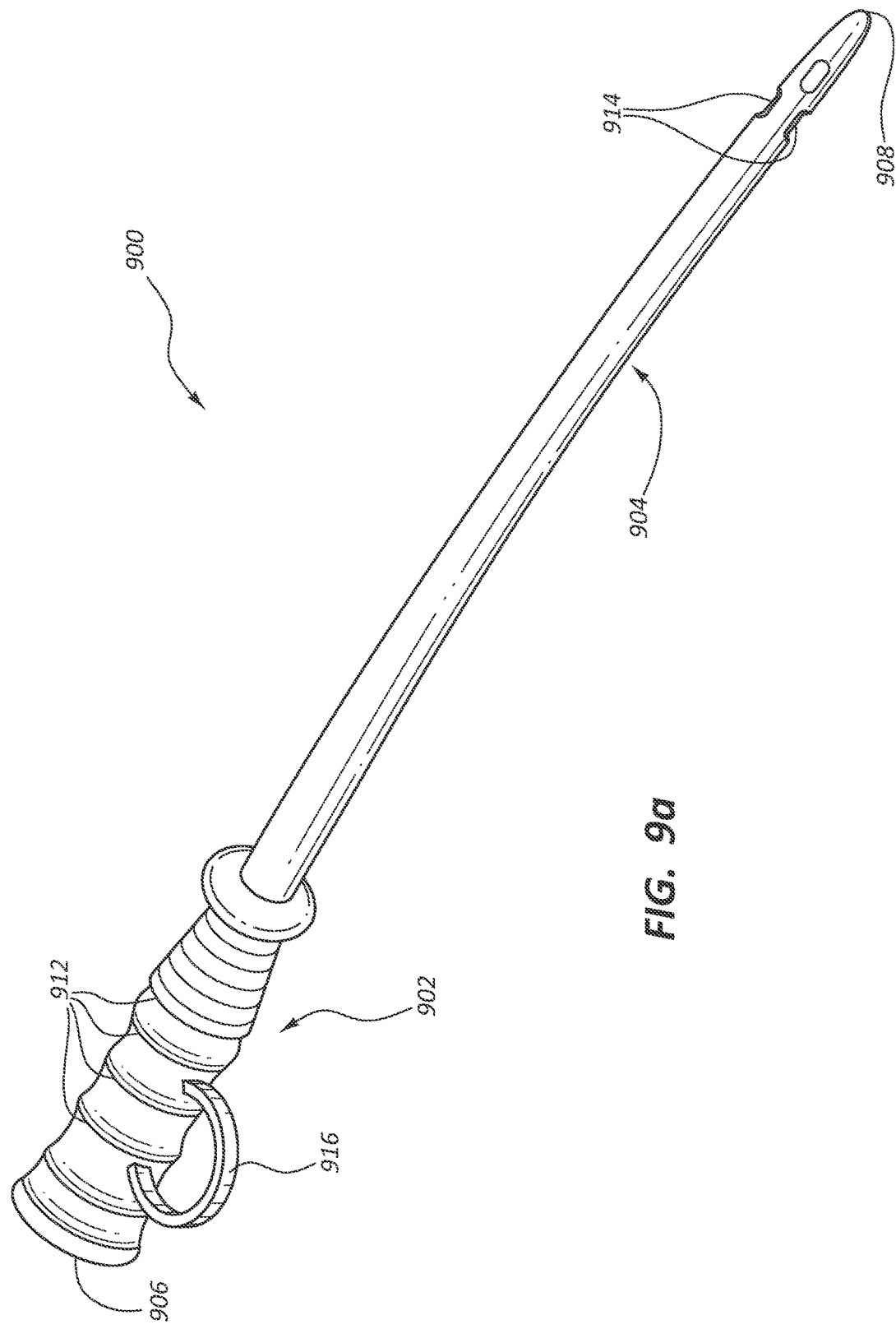
FIG. 9a provides a schematic illustrating a urinary catheter including a third loop for manipulating the catheter in accordance with some embodiments.
Figure 9B:
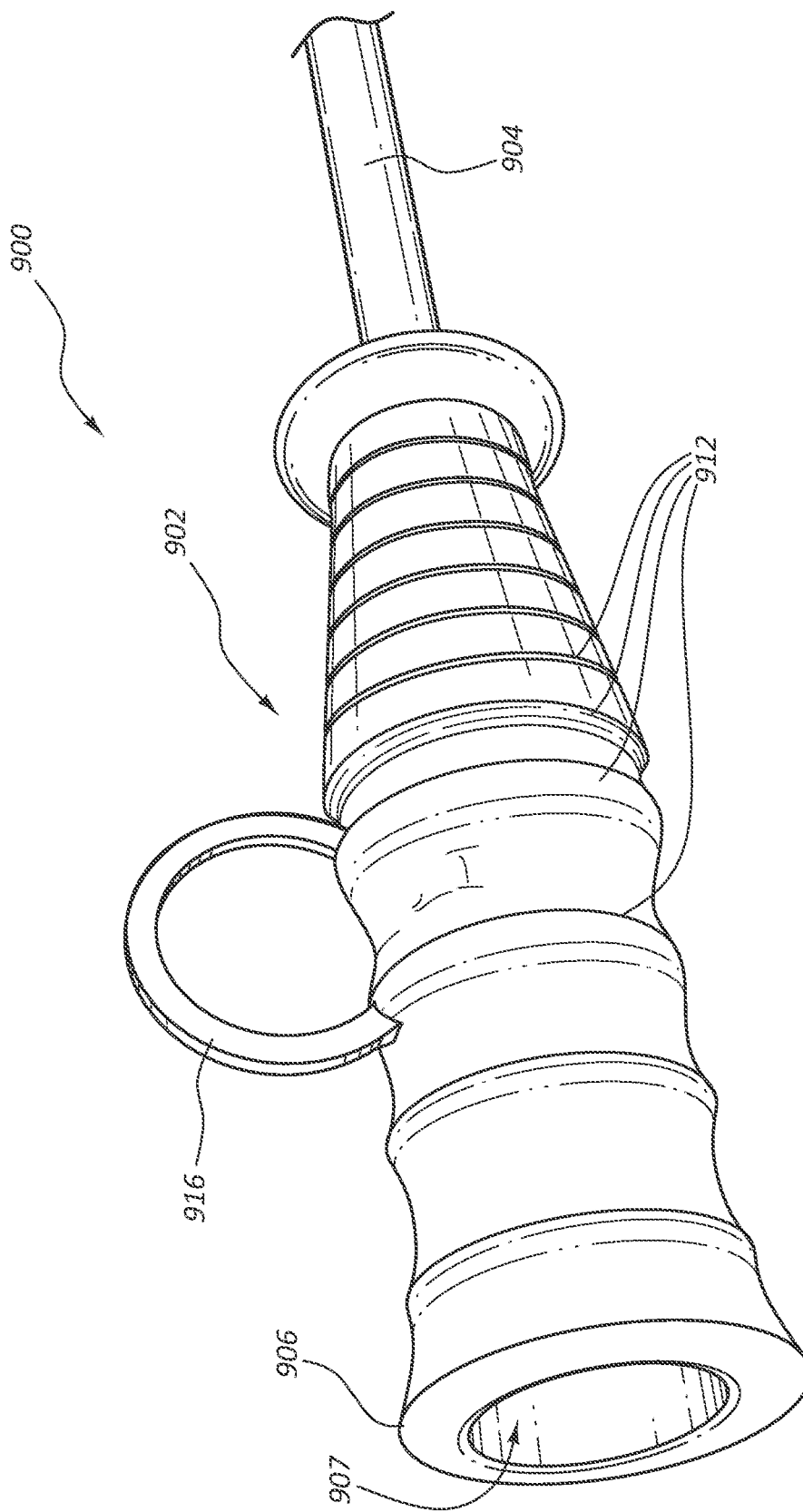
FIG. 9b provides a schematic illustrating a close-up view of a handle of the catheter of FIG. 9a in accordance with some embodiments.

Referring now to FIGS. 8a-8d, 9a, and 9b, schematics are provided illustrating urinary catheters including loops for manipulating the catheters in accordance with some embodiments. Such loops are useful in manipulating the catheters during at least catheterization processes, especially for individuals with limited dexterity or lacking full control of their fingers for such catheterization processes.

Like the urinary catheter 100, a urinary catheter 800, 801, 900 includes a catheter shaft 804, 904 attached to a handle 802, 902 about a proximal end portion of the catheter 800, 900. With respect to the catheter shaft 802, 902, it includes openings 814, 914 in a distal end portion of the catheter shaft 804, 904 that are in fluid communication with a lumen (see, for example, lumen 150 of catheter 100 of FIG. 3b) that extends through the catheter shaft 804, 904 and the handle 802, 902. The catheter shaft 804, 904 includes opposing eyelets 814, 914 proximate a tip 808, 908 of the catheter shaft 804, 904 in fluid communication with an opening 807, 907 in a proximal end of the handle 802, 902 by way of the lumen of the catheter 800, 900 that connects the catheter shaft 804, 904 and the handle 802, 902. As shown, the opposing eyelets 814, 914 can include, but are not limited to, at least two pairs of eyelets 814, 914 longitudinally staggered along a length of the catheter shaft 804, 904, wherein the eyelets 814, 914 are circumferentially positioned about 90 degrees apart in a non-overlapping configuration. In other words, the opposing eyelets 814, 914 can include at least two pairs of staggered eyelets 814, 914 that are staggered along a length of the catheter shaft 804, 904 and offset by about 90 degrees around the catheter shaft 804, 904 in a non-overlapping configuration. With respect the handle 802, 902, it includes a funnel-like shape 806, 906 at a proximal end thereof adapted to connect to drain bags, extension tubes, or the like. The handle 802, 902 further includes a plurality of ridges 812, 912 configured to facilitate gripping the handle 802, 902 by an individual, as well as one or more of the loops 816, 817, 916 useful in manipulating the catheter 800, 801, 900 during at least catheterization processes.

With respect to the one or more loops 816, 817, 916, such loops are integral with the handle 802, 902 such as molded with the handle 802, 902 in order to provide the loops 816, 817, 916 with a structural integrity strong enough to withstand pulling and tugging on the loops 816, 817, 916 during a catheterization process. The one or more loops 816, 916 of the catheter 800, 900 are configured such that a first plane including a transverse cross-section of the handle 802, 902 is orthogonal to a second plane including at least one of the one or more loops 816, 916 or an opening of the one or more loops 816, 916. Such a configuration enables right or left handed individuals alike to perform catheterization processes with catheters like the catheter 800, 900, wherein the handle 802, 902 rests in a hand of an individual (e.g., a patient or a caregiver) while the one or more loops 816, 916 respectively receive one or more fingers of the individual. Alternatively, the foregoing first plane and second plane can be oblique to each other in some embodiments to provide a left or right handedness to the catheter 800, 900. That said, the one or more loops 817 of the catheter 801 are configured such that the first plane including the transverse cross-section of the handle 802 is parallel to a second plane including at least one of the one or more loops 817 or an opening of the one or more loops 817. As such, the one or more loops 816, 817, 916 can be designed with any of a number of configurations including the foregoing configurations and mixtures thereof to accommodate different needs.

As used herein a "loop" includes an extension of the handle 802, 902 of the catheter 800, 801, 900 configured to receive a finger of an individual such as during a catheterization process for manipulating the catheter 800, 801, 900. Such a loop includes the loop 816 of the catheter 800 of FIGS. 8a and 8b, which loop 816 is a ring attached to the handle 802 of the catheter 800 by a tab extension 818 of the handle, which ring and the tab extension 818, together, are an integral loop of the handle 802. Such a loop also includes the loop 817 of the catheter 801 of FIGS. 8c and 8d, which loop 817 is a ring attached to the handle 802 of the catheter 801 by a tab extension 819 of the handle, which ring and the tab extension 819, together, are an integral loop of the handle 802, albeit of a different orientation than that of the catheter 800. Such a loop also includes the loop 916 of the catheter 900 of FIGS. 9a and 9b, which loop 916 need not, but can, include a tab extension of the handle such as the tab extension 818 of the catheter 800.

The catheter 800, 801, 900 includes, in some embodiments, a hydrophilic base coating including, for example, PAA over the catheter shaft, a hygroscopic outer coating including, for example, a hydrogel over the catheter shaft, or a combination of the hygroscopic outer coating over the hydrophilic base coating over the catheter shaft. Such coatings are described herein for the catheter 100. For example, the hydrophilic base coating over the catheter shaft can be a base coating of PAA in a range of 0.2 wt % to 3 wt %, glycerin in a range of 15 wt % to 25 wt %, water in a range of 20 wt % to 30 wt %, and PEG 400 in a range of 40 wt % to 60 wt %. The hydrophilic base coating can alternatively be a base coating of PAA in a range of 0.1 wt % to 2.5 wt %, water in a range of 10 wt % to 45 wt %, and PEG in a range of 20 wt % to 65 wt %. For example, the hygroscopic outer coating over the catheter shaft can be an outer coating of a hydrogel in a range of 20 wt % to 30 wt %, glycerin in a range of 20 wt % to 30 wt %, and PEG 400 in a range of 40 wt % to 60 wt %. The hygroscopic outer coating can alternatively be an outer coating of a hydrogel in a range of 20 wt % to 30 wt %, glycerin in a range of 40 wt % to 60 wt %, and PEG 300 in a range of 20 wt % to 30 wt %. The hygroscopic outer coating can alternatively be an outer coating of a hydrogel in a range of 10 wt % to 35 wt %, glycerin in a range of 25 wt % to 75 wt %, PEG 300 in a range of 25 wt % to 65 wt %, and PEG 400 in a range of 25 wt % to 50 wt %. The hygroscopic outer coating can alternatively be an outer coating of a hydrogel in a range of 15 wt % to 35 wt %, water in a range of 10 wt % to 45 wt %, and PEG 400 in a range of 20 wt % to 75 wt %. The hygroscopic outer coating can alternatively be an outer coating of a hydrogel in a range of 22 wt % to 26 wt %, water in a range of 25 wt %, and PEG 400 is in a range of 49 wt % to 53 wt %. In addition, the catheter 800, 801, 900 can further include a UV-cured silicone film over at least a portion of the hydrophilic base coating, the hygroscopic outer coating, or the combination of the hygroscopic outer coating and the hydrophilic base coating as described herein for the catheter 100.

Like the catheter 100, the catheter 800, 801, 900 can be part of a catheter package wherein packaging (e.g., packaging 200 of FIGS. 5-7) of the catheter package includes an adhesive pull tab (e.g., adhesive pull tab 222 of FIGS. 5-7) over a perforated area (e.g., perforated area 224 of FIGS. 4a-4c and 7) of the packaging configured to expose the catheter 800, 801, 900 disposed in the packaging when the pull tab is pulled.

Individuals who are confined to wheelchairs based on injuries that need to use catheters such as intermittent catheters to void their bladders often do not have full control of their fingers as needed to catheterize themselves in a consistent manner. The one or more loops 816, 817, 916, of the catheter 800, 801, 900 provides those individuals independence by way of slipping one or more fingers respectively into the one or more loops 816, 817, 916 of the catheter 800, 801, 900 to help such individuals better manipulate the catheter 800, 801, 900 for insertion and removal during a catheterization process. Thus, the one or more loops 816, 817, 916 of the catheter 800, 801, 900 provides those (e.g., patients, caregivers, consumers, etc.) with limited dexterity a way to use as little as a single finger to manipulate and the catheter 800, 900 (e.g., an intermittent catheter) in a more convenient and controllable fashion.

While the invention has been described in terms of particular variations and illustrative figures, those of ordinary skill in the art will recognize that the invention is not limited to the variations or figures described. Those of ordinary skill in the art will recognize that the invention is not limited to the application of catheters but may be applied to any device that requires similar lubrication. In addition, where methods and steps described above indicate certain events occurring in a certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Further, the features described in one embodiment may generally be combined with features described in other embodiments. Therefore, to the extent there are variations of the invention, which are within the spirit of the disclosure or equivalent to the inventions found in the claims, it is the intent that this patent will cover those variations as well.

What is claimed is:

1. A urinary catheter, comprising:
   a handle including:
      a plurality of ridges designed for gripping the handle; and
      one or more loops integral with the handle designed for manipulating the urinary catheter; and
   a catheter shaft attached to the handle, the catheter shaft including:
      a catheter tip;
      a lumen; and
      a plurality of eyelets proximate the catheter tip, the plurality of eyelets in fluid communication with an opening in a proximal end of the handle by way of the lumen.

2. The urinary catheter according to claim 1, wherein a first plane including a transverse cross-section of the handle is orthogonal to a second plane including at least one opening of the one or more loops.

3. The urinary catheter according to claim 1, wherein the handle is configured to rest in a hand of a patient or a caregiver while the one or more loops respectively receive one or more fingers of the patient or the caregiver.

4. The urinary catheter according to claim 1, wherein the one or more loops are respectively one or more rings, each attached to the handle by a tab extension of the handle.

5. The urinary catheter according to claim 1, wherein the plurality of eyelets include at least two pairs of staggered eyelets staggered along a length of the catheter shaft and offset by about 90 degrees around the catheter shaft in a non-overlapping configuration.

6. The urinary catheter according to claim 1, further comprising:
   a hydrophilic base coating over the catheter shaft, a base coating of polyacrylic acid (PAA) in a range of 0.2 wt % to 3 wt %, glycerin in a range of 15 wt % to 25 wt %, water in a range of 20 wt % to 30 wt %, and polyethylene glycol (PEG) 400 in a range of 40 wt % to 60 wt %.

7. The urinary catheter according to claim 1, further comprising:
   a hydrophilic base coating over the catheter shaft, a base coating of polyacrylic acid (PAA) in a range of 0.1 wt % to 2.5 wt %, water in a range of 10 wt % to 45 wt %, and polyethylene glycol (PEG) in a range of 20 wt % to 65 wt %.

8. The urinary catheter according to claim 1, further comprising:
   a hygroscopic outer coating over the catheter shaft, an outer coating of a hydrogel in a range of 20 wt % to 30 wt %, glycerin in a range of 20 wt % to 30 wt %, and polyethylene glycol (PEG) 400 in a range of 40 wt % to 60 wt %.

9. The urinary catheter according to claim 1, further comprising:
   a hygroscopic outer coating over the catheter shaft, an outer coating of a hydrogel in a range of 20 wt % to 30 wt %, glycerin in a range of 40 wt % to 60 wt %, and polyethylene glycol (PEG) 300 in a range of 20 wt % to 30 wt %.

10. The urinary catheter according to claim 1, further comprising:
    a hygroscopic outer coating over the catheter shaft, an outer coating of a hydrogel in a range of 10 wt % to 35 wt %, glycerin in a range of 25 wt % to 75 wt %, polyethylene glycol (PEG) 300 in a range of 25 wt % to 65 wt %, and PEG 400 in a range of 25 wt % to 50 wt %.

11. The urinary catheter according to claim 1, further comprising:
    a hygroscopic outer coating over the catheter shaft, an outer coating of a hydrogel in a range of 15 wt % to 35 wt %, water in a range of 10 wt % to 45 wt %, and polyethylene glycol (PEG) 400 in a range of 20 wt % to 75 wt %.

12. The urinary catheter according to claim 1, further comprising:
    a hygroscopic outer coating over the catheter shaft, an outer coating of a hydrogel in a range of 22 wt % to 26 wt %, water at approximately 25 wt %, and polyethylene glycol (PEG) 400 is in a range of 49 wt % to 53 wt %.

* * * * *